(12) United States Patent
Rhee et al.

(10) Patent No.: US 7,682,607 B2
(45) Date of Patent: Mar. 23, 2010

(54) WNT AND FRIZZLED RECEPTORS AS TARGETS FOR IMMUNOTHERAPY IN HEAD AND NECK SQUAMOUS CELL CARCINOMAS

(75) Inventors: Chae-Seo Rhee, Seoul (KR); Malini Sen, La Jolla, CA (US); Christina Wu, San Diego, CA (US); Lorenzo M. Leoni, San Diego, CA (US); Maripat Corr, San Diego, CA (US); Dennis A. Carson, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1656 days.

(21) Appl. No.: 10/381,636

(22) PCT Filed: May 1, 2002

(86) PCT No.: PCT/US02/13802

§ 371 (c)(1),
(2), (4) Date: Mar. 5, 2004

(87) PCT Pub. No.: WO02/088081

PCT Pub. Date: Nov. 7, 2002

(65) Prior Publication Data
US 2004/0203003 A1     Oct. 14, 2004

Related U.S. Application Data

(60) Provisional application No. 60/287,995, filed on May 1, 2001.

(51) Int. Cl.
*A61K 39/395* (2006.01)
(52) U.S. Cl. .................................... 424/130.1
(58) Field of Classification Search .................. None
See application file for complete search history.

(56) References Cited

U.S. PATENT DOCUMENTS

| | | |
|---|---|---|
| 4,458,066 A | 7/1984 | Caruthers et al. |
| 4,683,192 A | 7/1987 | Nishiyama |
| 4,683,202 A | 7/1987 | Mullis |
| 4,800,159 A | 1/1989 | Mullis et al. |
| 4,965,188 A | 10/1990 | Mullis et al. |
| 5,250,203 A | 10/1993 | Denis et al. |
| 5,677,171 A | 10/1997 | Hudziak et al. |
| 5,720,937 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,824,789 A | 10/1998 | Van Den Berg |
| 5,837,538 A | 11/1998 | Scott et al. |
| 5,851,984 A * | 12/1998 | Matthews et al. ............. 514/2 |
| 5,994,098 A | 11/1999 | Hu et al. |
| 6,008,000 A | 12/1999 | Margolskee |
| 6,043,053 A | 3/2000 | Barnes |
| 6,100,060 A | 8/2000 | Barnes et al. |
| 6,133,232 A | 10/2000 | De Robertis et al. |
| 6,165,748 A | 12/2000 | Racie et al. |
| 6,165,751 A | 12/2000 | Barnes |
| 6,183,968 B1 | 2/2001 | Bandman et al. |
| 6,291,516 B1 | 9/2001 | Dudek et al. |
| 6,297,030 B1 | 10/2001 | Barnes et al. |
| 6,307,019 B1 | 10/2001 | Constantini et al. |
| 6,387,657 B1 | 5/2002 | Botstein et al. |
| 6,403,325 B1 | 6/2002 | Kosik et al. |
| 6,433,155 B1 | 8/2002 | Umansky et al. |
| 2002/0173461 A1 * | 11/2002 | Pennica et al. ................ 514/12 |
| 2002/0187502 A1 | 12/2002 | Waterman et al. |
| 2003/0044409 A1 | 3/2003 | Carson et al. |
| 2003/0203416 A1 | 10/2003 | Staudt et al. |

FOREIGN PATENT DOCUMENTS

| | | |
|---|---|---|
| EP | 1 001 023 A | 5/2000 |
| JP | 2004-051557 A | 2/2004 |
| WO | WO 89/07142 | 8/1989 |
| WO | WO 92/17585 | 10/1992 |
| WO | WO 97/39357 | 10/1997 |
| WO | WO 97/41854 | 11/1997 |
| WO | WO 97/48275 | 12/1997 |
| WO | WO 98/13493 | 4/1998 |
| WO | WO 98/16641 | 4/1998 |
| WO | WO 98/23730 | 6/1998 |
| WO | WO 98/46755 | 10/1998 |
| WO | WO 98/54325 | 12/1998 |
| WO | WO 99/02679 | 1/1999 |
| WO | WO 99/26960 | 6/1999 |
| WO | WO 99/29719 | 6/1999 |
| WO | WO 99/38966 | 8/1999 |
| WO | WO 99/43804 | 9/1999 |
| WO | WO 99/50385 | 10/1999 |

(Continued)

OTHER PUBLICATIONS

Freshney (Culture of Animal Cells, A Manual of Basic Technique, Alan R. Liss, Inc., 1983, New York, p. 4).*

(Continued)

*Primary Examiner*—Christopher H Yaen
(74) *Attorney, Agent, or Firm*—McDermott Will & Emery LLP

(57) ABSTRACT

The diverse receptor-ligand pairs of the Wnt and frizzled (Fzd) families play important roles during embryonic development, and thus may be overexpressed in cancers that arise from immature cells. The mRNA levels and expression levels of 5 Wnt (Wnt-1, 5a, 7a, 10b, 13) and 2 Fzd (Fzd-2, 5) genes in 10 head and neck squamous carcinoma cell lines (HNSCC) were investigated. In addition, anti-Wnt-1 antibodies were used to study the Wnt/Fzd signalling pathway. These results indicate that HNSCC cell lines overexpress one or more Wnt and Fzd genes, and the growth and survival of a subset of HNSCC may depend on the Wnt/Fzd pathway. Therefore, The Wnt and Fzd receptors may be useful targets for immunotherapy of this common cancer.

6 Claims, 17 Drawing Sheets

FOREIGN PATENT DOCUMENTS

| | | |
|---|---|---|
| WO | WO 99/63052 | 12/1999 |
| WO | WO 00/00491 | 1/2000 |
| WO | WO 00/03037 | 1/2000 |
| WO | WO 00/12117 | 3/2000 |
| WO | WO 00/17326 | 3/2000 |
| WO | WO 00/20039 | 4/2000 |
| WO | WO 00/29575 | 5/2000 |
| WO | WO 00/30162 | 5/2000 |
| WO | WO 00/38709 | 7/2000 |
| WO | WO 01/02440 A1 | 1/2001 |
| WO | WO 01/03743 A1 | 1/2001 |
| WO | WO 01/04306 A1 | 1/2001 |
| WO | WO 01/12808 | 2/2001 |
| WO | WO 01/19855 | 3/2001 |
| WO | WO 01/32708 | 5/2001 |
| WO | WO 01/38353 | 5/2001 |
| WO | WO 01/74856 | 10/2001 |
| WO | WO 01/75067 A2 | 10/2001 |
| WO | WO 01/83543 A1 | 11/2001 |
| WO | WO 02/16620 A2 | 2/2002 |
| WO | WO 02/24733 A2 | 3/2002 |
| WO | WO 02/31148 | 4/2002 |
| WO | WO 02/31210 | 4/2002 |
| WO | WO 02/44378 | 6/2002 |
| WO | WO 02/059377 A2 | 8/2002 |
| WO | WO 02/088081 A2 | 11/2002 |

OTHER PUBLICATIONS

Dermer (Bio/Technology, 1994, 12:320).*
"Membrane Receptors: Frizzled and Related Proteins"; *Santa Cruz Biotechnology, Online Catalogue*; Retrieved from the Internet: http://www.scbt.com/catalog/action.lasso?-database=intros2003&-layout=main&-response=toc_subsection.html&-recordID=38067& -token.order_id=1630401&-search; Retrieved on Nov. 16, 2003.
Aoki et al.; "Nuclear endpoint of Wnt signaling: Neoplastic transformation induced by transactivating lymphoid-enhancing factor 1" *Proc. Nat'l Acad. Sci.* USA 96:139-144 (1999).
Bui et al.; "A novel human *Wnt* gene, *WNT10B*, maps to 12q13 and is expressed in human breast carcinomas" *Oncogene*; 1997; pp. 1249-1253; vol. 14.
Bui et al.;"Expression and hormone regulation of Wnt2, 3, 4, 5a, 7a, 7b and 10b in normal human endometrium and endometrial carcinoma" *Br. J. Canc.*; 1997; pp. 1131-1136; vol. 75, No. 8.
Cadigan et al.; "Wnt signaling: a common theme in animal development" *Genes Dev.*; 1997; 3286-3305; vol. 11.
Chan et al.; "A common human skin tumour is caused by activating mutations in β-catenin" *Nat Genet*; 1999; pp. 410-413; vol. 21.
Chen et al.; Wnt-1 Signaling Inhibits Apoptosis by Activating β-Catenin/T Cell Factor-mediated Transcription *J Cell Biol*; 2001; pp. 87-96; vol. 152.
De La Coste et al.; "Somatic mutations of the β-catenin gene are frequent in mouse and human hepatocellular carcinomas" *Proc.Nat'l Acad Sci. USA*; 1998; pp. 8847-8851; vol. 95.
Hamilton et al.; "The Molecular Basis of Turcot's Syndrome" *N. Engl. J Med.*; 1995; pp. 839-847; vol. 332.
Huguet et al.; "Differential Expression of Human *WNT* Genes 2, 3, 4, and 7B in Human Breast Cell Lines and Normal Disease States of Human Breast Tissue" *Cancer Research*; 1994; pp. 2615-2621; vol. 54.
Ikeda, "Mutational analysis of the *CTNNB1* (β-catenin) gene in human endometrial cancer: Frequent mutations at condon 34 that cause nuclear accumulation" *Oncol Rep*; 2000; pp. 323-326; vol. 7.
Iozzo et al.; "Aberrant Expression of the Growth Factor *Wnt-5A* in Human Malignancy" *Canc. Res.*; 1995; pp. 3495-3499; vol. 55.
Katoh et al.; Cloning, expression and chromosomal localization of *Wnt-13*, a novel member of the *Wnt* gene family *Oncogene*; 1996; pp. 873-876; vol. 13.
Katoh; "Frequent up-regulation of *WNT2* in primary gastric cancer and colorectal cancer" *J. Oncol.*; 2001; pp. 1003-1007; vol. 19, No. 5.

Kirikoshi et al.; "Expression of *WNT14* and *WNT14B* mRNAs in human cancer, up-regulation of *WNT14* by IFN and up-regulation of *WNT14B* by β-estradiol" *J. Oncol.*; 2001; pp. 1221-1225; vol. 19.
Kirikoshi et al.; "Expression of *WNT10A* in human cancer" *Int. J. Oncol.*; 2001; pp. 997-1001; vol. 19, No. 5.
Kirikoshi et al.; "Expression of *WNT7A* in human normal tissues and cancer, and regulation of *WNT7A* and *WNT7B* in human cancer" *Int. J. Oncol.*; 2002; pp. 895-900; vol. 21.
Kirikoshi et al.; "*WNT10A* and *WNT6*, Clustered in Human Chromosome 2q35 Region with Head-to-Tail Manner, Are Strongly Coexpressed in SW480 Cells" *BBRC*; 2001; pp. 798-805; vol. 283.
Kramps et al.;"Wnt/Wingless Signaling Requires BCL9/Leglass-Mediated Recruitment of Pygopus to the Nuclear β-Catenin-TCF Complex" *Cell*; 2002; p. 4760; vol. 109.
Leethanakul et al.;"Distinct pattern of expression of differentiation and growth-related genes in squamous cell carcinomas of the head and neck revealed by the use of laser capture microdissection and cDNA arrays", *Oncogene*; 2000; pp. 3220-3224; vol. 19.
Lejeune et al.; "*Wnt5a* Cloning, Expression, and Up-Regulation in Human Primary Brest Cancers" *Clin. Canc. Res*; 1995; pp. 215-222; vol. 1.
Lo Muzio et al.; "WNT-1 expression in basal cell carcinoma of head and neck. An immunohistochemical and confocal study with regard to the intracellular distribution of beta-catenin" *Anticancer Res.*; 2002; pp. 565-576; vol. 22, No. 2A.
Malik, J. H. et al.; "Structure and Expression of a Novel Frizzled Gene Isolated from the Developing Mouse Gut"; *Biochemical Journal* 2000; pp. 829-834; vol. 349; Portland Press, London, GB.
Mao et al.; "Kremen proteins are Dickkopf receptors that regulate *Wnt/b*-catenin signaling" *Nature*; 2002; pp. 664-667; vol. 417:6889.
McWhirter et al.; "Oncogenic homeodomain transcription factor E2A-Pbx1 activates a novel WNT gene in pre-B acute lymphoblastoid leukemia" *Proc. Natl., Acad. Sci.*; 1999; 11464-11469; vol. 96.
Miller et al.; "Mechanism and fuction of signal transduction by the Wnt/ β-catenin and Wnt/Ca2+ pathways" *Oncogene*; 1999; pp. 7860-7872; vol. 18.
Nusse et al.; "Many Tumors Induced by the Mouse Mammary Tumor Virus Contain a Provirus Integrated in the Same Region of the Host Genome" *Cell*; 1982; pp. 99-109; vol. 31.
Palacios et al.; "Mutations in the β-Catenin Gene (*CTNNB1*) in Endometrioid Ovarian Carcinomas" *Cancer Res.*; 1998; pp. 1344-1347; vol. 58.
Polakis, P. "Wnt Signaling and Cancer"; *Genes and Development*; Aug. 1, 2000; pp. 1837-1851; vol. 14; No. 15; Cold Spring Harbor Press, New York, NY, USA.
Rhee et al.; "Wnt and frizzled receptors as potential targets for immunotherapy in head and neck squamous cell carcinomas" *Oncogene*; 2002; pp. 6598-6605; vol. 21.
Rimm et al.; "Frequent Nuclear/Cytoplasmic Localization of β-CatenIn without Exon 3 Mutations in Malignant Melanoma" *Am J. Pathol*; 1999; pp. 325-329; vol. 154.
Sagara, N. et al.; "Molecular Cloning, Differential Expression, and Chromosomal Localization of Human Frizzled-1, Frizzled-2, and Frizzled-7"; *Biochemical and Biophysical Research Communications*; 1998; pp. 117-122; vol. 252; Academic Press Inc., Orlando, FL, USA.
Saitoh et al.; "Expression and regulation of *WNT8A* and *WNT8B* mRNAs in human tumor cell lines: Up-regulation of *WNT8B* mRNA by β-estradiol in MCF-7 cells, and down-regulation of *WNT8A* and *WNT8B* mRNAs by retinoic acid in NT2 cells" *J. Oncol.*; 2002; pp. 999-1003; vol. 20, No. 5.
Shimizu et al.; Transformation by Wnt Family Proteins Correlates with Regulation of β-Catenin *Cell Growth Differ*; 1997; pp. 1349-1358; vol. 8.
Shou et al.; "Human Dkk-1, a gene encoding a Wnt antagonist, responds to DNA damage and its overexpression sensitizes brain tumor cells to apaptosis following alkylation damage of DNA" *Oncogene*; 2002; pp. 878-889; vol. 21.
Tanaka, S. et al.; "A Novel Frizzled Gene Identified in Human Esophageal Carcinoma Mediates APC/Beta-Catenin Signals"; *Proceedings of the National Academy of Science*; Aug. 1998; pp. 10167-10169; vol. 95; Washington, USA.

Tokuhara, M. et al.; "Molecular Cloning of Human—Frizzled—-6"; *Biochemical and Biophysical Research Communications*; 1998; XP002074753; Academic Press Inc., Orlando, FL, USA.
Van De Wetering et al.; "WNT Signaling and Lymphocyte Development" *Cell*; 2002; pp. S13-S19; vol. 109.
Van Gijn, Marielle E. et at. "Overexpression of Components of the Frizzled-Dishevelled Cascade Results in Apoptotic Cell Death, Mediated by Beta-Catenin"; *Experimental Cell Research*; Apr. 15, 2001; pp. 46-53; vol. 265, No. 1.
Weeraratna, Ashani T. et al.; "Wnt5a Signaling Directly Affects Cell Motility and Invasion of Metastatic Melanoma"; *Cancer Cell*; Apr. 2002; pp. 279-288; vol. 1, No. 3.
Wong et al.; "Expression of frizzled-related protein and Wnt-signalling molecules in invasive human breast tumours" *J. Pathol.*; 2002; pp. 145-153; vol. 196.
Yang-Snyder et al.; A *frizzled* homolog functions in a vertebrate *Wnt* signaling pathway *Curr Biol*; 1996; pp. 1302-1306; vol. 6.
Zhou et al.; "Up-Regulation of Human Secreted Frizzled Homolog in Apoptosis and its Down-Regulation in Breast Tumors" *Int J. Cancer*; 1998; pp. 95-99; vol. 78.
Chung et al., "Regulation of leukemic cell adhesion, proliferation, and survival by beta-catenin," *Blood* 100(3):982-9990 (2002).
Katoh M., "Molecular cloning and characterization of human WNT3," *Int. J. of Oncology* 19(5):977-982 (2001).
Katoh M., "WNT3-WNT14B and WNT3A-WNT14 gene clusters," *Int. J. of Mol. Med.* 9(6):579-584 (2002).
Lu et al., "Activation of the Wnt signaling pathway in chronic lymphocytic leukemia," *PNAS of USA* 101(9):3118-3123 (2004).
Reya et al., "Wnt signaling regulates B lymphocyte proliferation through a LEF-1 dependent mechanism," *Immunity* 13(1):15-24 (2000).
Rhee et al., "Wnt and frizzled receptors as potential targets for immunotherapy in head and neck squamous cell carcinomas," *Oncogene* 21(43):6598-6605 (2002).
Rosenwald et al., "Relation of gene expression phentoype to immunoglobulin mutation genotype in B cell chronic lymphocytic leukemia," *J. of Exp. Med.* 194(11):1639-1647 (2001).
Aberle et al., J. Cell Sci. (1994) 107:3655-3663.
Adler et al., Molecular Vision (1999) 5:31.
Akiyama et al., Science (1986) 232: 1644-1646.
Ausubel et al., Molecular cloning of PCR roducts, in: Short Protocols in Molecular Biology, 3rd Ed., John Wiley & Sons, Inc., New York, pp. 15-32 (1997).
Beaucage et al., Tetrahedron letters (1981) 22: 1859-1962.
Behrens et al., Nature (1996) 382: 638-642.
Bhanot et al., Nature (1996) 382: 225-230.
Birney et al., Nature (2001) 409: 827-828.
Brown et al., Meth. Enzymol. (1979) 68: 109.
Chae-Seo et al., "Wnt and frizzled receptors as potential targets for immunotherapy in head and neck squamous cell carcinomas" *Oncogene* 21:6598-6605 (2002).
Chan et al., J. Immunol. (2001) 166: 3061-3066.
Cho et al., Nat. Biotechnol. (2000) 18: 509-514.
Corr et al., J. Exp. Med. (1996) 184: 1555-1560.
Corr et al., J. Immunol. (1997) 4999-5004.
Corr et al., J. Immunol. (1999) 163: 4721-4727.
Coussens et al., Science (1985) 230: 1132-1139.
Cruthers, Science (1985) 230: 281-285.
Dakappagari et al., Cancer Res. (2000) 60: 3782-3789.
Dandliker et al., J. Exp. Med. (1965) 122: 1029.
Dennis et al., J. Cell. Sci. (1999) 112(Pt. 21): 3815-3820.
Ehricht et al., Eur. J. Biochem. (1997) 243: 358-364.
Fahrlander et al., Bio/Technology (1988) 6: 1165-1168.
Fendly et al., J. Biol. Response Mol. (1990) 9: 449-455.
Fendly et al., Cancer Res. (1990) 50: 1550-1558.
Finch et al., Proc. Natl. Acad. Sci. USA (1997) 94(13): 6770-6775.
FRP/FrzB Genes and Interactions with Wnts, http://www.stanford.edu/~rnusse/frizzleds/frp.html.
FRP/FrzB Genes and Interactions with Wnts, http://www.stanford.edu/~rnusse/frizzleds/frp.html.
Genini et al., Blood (2000) 96(10): 3537-3543.
Hashimoto et al., Arthritis Rheum. (1998) 41(9): 1632-1638.
He et al., Science (1997) 275: 1652-1654.
He et al., Science (1998) 281: 1509-1512.
Henderson et al., Clin. Chem. (1986) 32: 1637-1641.
Hoang et al., Dev. Dyn. (1998) 212(3): 364-372 (Abstract).
Hoang et al., The Journal of Biological Chemistry (1996) 271(42): 26131-26137.
Hoschuetzky et al., J. Cell. Biol. (1994) 127: 1375-1380.
Hudziak et al., Mol. Cell. Biol. (1989) 9: 1165-1172.
Hunter, Cell (1997) 88: 333-346.
Huse et al., Science (1989) 246: 1275-1281.
James et al., Osteoarthritis and Cartilage (2000) 8: 452-463.
Jones et al., Investigative Opthalmology & Visual Science (2000) 41(6): 1297-1301.
Jones, Neuroreport (2000) 11(18): 3963-3967 (Abstract).
Katoh et al., Biochem. Biophys. Res. Commun. (2000) 275(1): 209-216 (Abstract).
Kim et al., Acta Otolaryngol. (1997) 117: 775-784.
Kim et al., Mech. Dev. (2001) 103(1-2): 167-172.
King et al., Science (1985) 229: 974-976.
Kirikoshi, Biochem. Res. Commun. (1999) 264(3): 955-961.
Kirikoshi, Biophys. Res. Commun. (2000) 27(1): 8-14.
Koike, Biochem. Biophys. Res. Commun. 262(1): 39-43, (1999).
Korinek et al., Science (1997) 275: 1784-1787.
Ku et al., Laryngoscope (1999) 109: 976-982.
Landis et al., CA Cancer J. Clin. (1999) 49: 8-31.
Laufer et al., Cell (1994) 79: 993-1003.
Li et al., J. Biol. Chem. (1999) 274: 129-134.
Loughlin et al., Rheumatology (2000) 39: 377-381.
Lotz et al., Osteoarthritis and Cartilage (1999) 7: 389-391.
Morin et al., Science (1997) 275: 1787-1790.
Muller et al., Histochem. Cell Biol. (1997) 108: 431-437.
Ng et al., Curr. Top. Dev. Biol. (1999) 41: 37-66.
Niswander et al., Cell (1993) 75: 579-587.
Niswander et al., Mol. Reprod. Dev. (1994) 39: 83-89.
Niswander et al., Nature (1994) 371: 609-612.
Nrang et al., Meth. Enzymol. (1979) 68:90.
Oellerich, J. Clin. Chem.Clin. Biochem. (1980) 18: 197-208.
O'Hern et al., Vaccine (1997) 16(15): 1761-1766.
Parkin et al., CA Cancer J. Clin. (1999) 49: 33-64.
Parr et al., Development (1993) 119: 247-261.
Paterson et al., Mol. Hum. Reprod. (1999) 5: 342-352.
Pietras et al., Oncogene (1994) 9: 1829-1838.
Radulovic et al., Cancer Res. (1991) 51: 6006-6009.
Ramsdell et al., Genet (1998) 14: 459-465.
Rattner et al., Proc. Natl. Acad. Sci. USA (1997) 94(7): 2859-2863 (Abstract).
Ravdin et al., Gene (1995) 159: 1927.
Riddle et al., Cell (1993) 75: 1401-1416.
Riddle et al., Cell (1995) 83: 631-640.
Roszmusz et al., J. Biol. Chem. (2001) (Abstract).
Rubenstein, Biochem. Biophys. Res. Comm. (1972) 47: 846-851.
Rubinfeld et al., Science (1996) 272: 1023-1026.
Rubinfeld et al., Science (1997) 275: 1790-1792.
Rulifson et al., Mol. Cell. (2000) 6(1): 117-126.
Sala, Biochem. Biophys. Res. Commun. (2000) 273(1): 27-34.
Sata et al., Science (1996) 273: 352-354.
Sen et al., Arthritis & Rheumatism (2001) 44(4): 772-781.
Sen et al., PNAS (2000) 97(6): 2791-2796.
Shtutman et al., Proc. Natl. Acad. Sci. USA (1999) 96: 5522-5527.
Singh et al., Am. J. Public Helath (2001) 91: 392-399.
Slamon et al., Science (1987) 235: 177-182.
Slamon et al., Science (1989) 244: 707-712.
Slamon et al., N. Engl. J. Med. (2001) 344: 783-792.
Sparks et al., Cancer Res. (1998) 58: 1130-1134.
Stone, Nature (1996) 384(6605): 129-134.
Takahashi et al., J. Rheumatol. (2000) 27(7): 1713-1720 (Abstract).
Umbhauer et al., Embo J. (2000) 19(18): 4944-4954 (Abstract).
Urdea et al., Nucleic Acids Symp. Ser. (1991) 24: 197-200.
Uren et al., J. Biol. Chem. (2000) 275: 4374-4382.
Venter et al., Science (2001) 291: 1304-1351.
Vinson et al., Nature (1987) 329: 549-551.
Vogel et al., Development (1996) 122: 1737-1750.
Vogel et al., Nature (1995) 378: 716-720.
Vogel et al., Development (1993) 119: 199-206.

Walker et al., Nucleic Acids Res. (1992) 20: 1691-1696.
Wang et al., Genomics (1999) 57(2): 235-248 (Abstract).
Wang, J. Biol. Chem. (1996) 271(8): 4468-4476.
Wang, Hum. Mol. Gen. (1997) 6(3): 465-472.
Whiteside et al., Clin. Cancer Res. (1998) 4: 1135-1145.
Wisdom, Clin. Chem. (1976) 22(8): 1243-1255.
Wodarz et al., Annu. Rev. Cell Dev. Biol. (1998) 14: 59-88.
Wnt Gene Homepage, http://www.stanford.edu/~rnusse/wntwindow.html.
Yasumura et al., Cancer Res. (1993) 53: 1461-1468.
Yost et al., Genes Dev. (1996) 10: 1443-1454.
Zhao, Genomics (1995) 27(2): 370-373.
Brown, "Wnt signaling in breast cancer: have we come full circle?", *Breast Cancer Research*, 2001, pp. 351-355, vol. 3(6).

Kirikoshi et al., "Molecular Cloning and Genomic Structure of Human *Frizzled*-3 at chromosome 8p21", *Biochemical and Biophysical Research Communications*, 2000, pp. 8-14, vol. 271.
Sakanaka et al., "Bridging of β-catenin and glycogen synthase kinase-3β a by Axin and inhibition of β-catenin-mediated transcription" *PNAS*, 1998, pp. 3020-3023, vol. 95.
Sampson et al., "Negative regulation of the Wnt-β catenin pathway by the transcriptional repressor HBP1", *The EMBO Journal*, 2001, pp. 4500-4511, vol. 20(16).
Tanner et al., "BAALC, the human member of a novel mammalian neuroectoderm gene lineage, is implicated in hematopoiesis and acute leukemia", *PNAS*, 2001, p. 13901-13905, vol. 98(24).

* cited by examiner

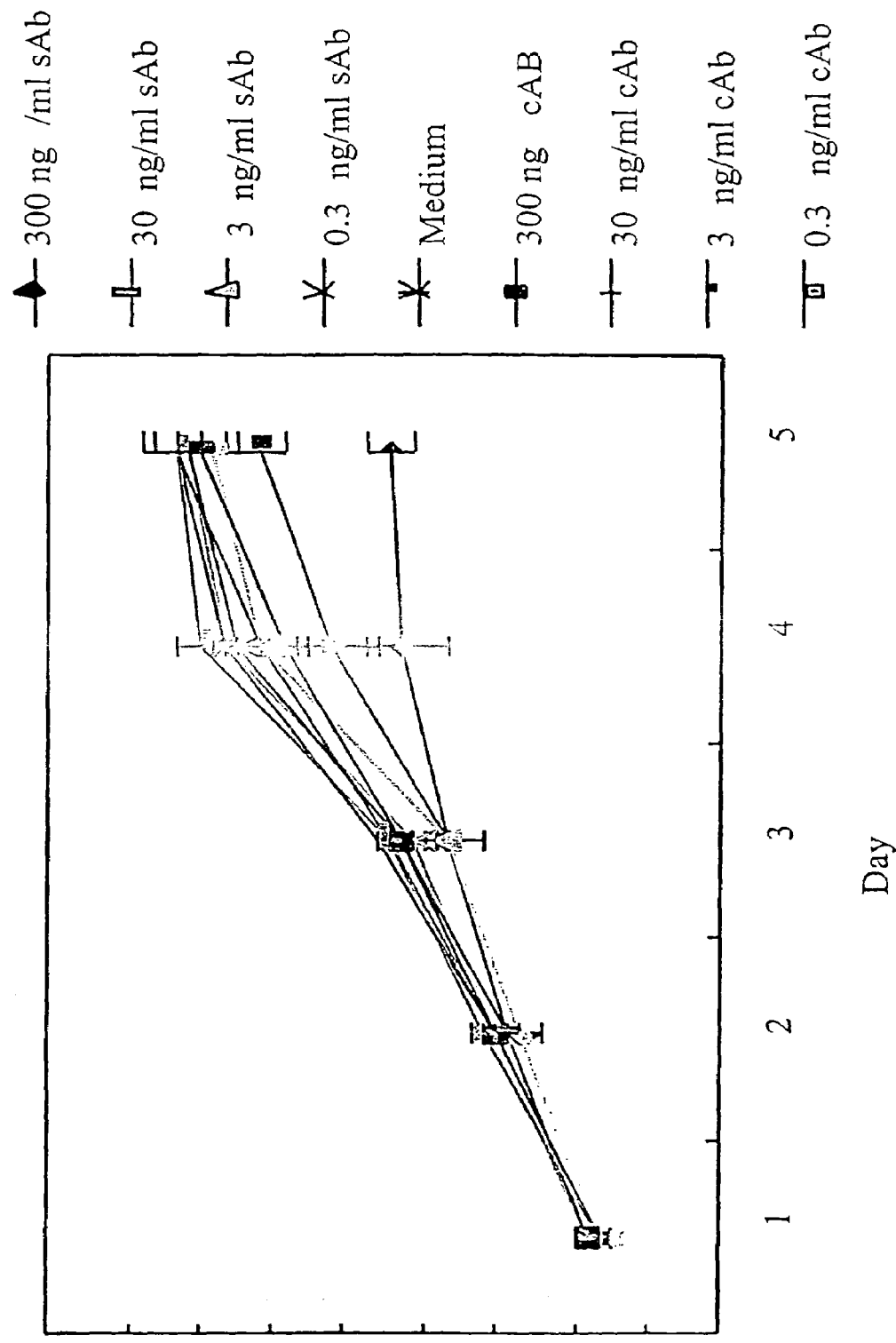
Figure 4B    Anti-Wnt 1

Figure 6

```
HFZ1   VGQNTSDKGT----PSLLPEFWTSNPQHGGGGHRG-------------------------------------------------------------GFPGGAG----ASERGKFSCPR
HFZ2   VGQNHSEDGA-----PALLTTAPPGLQPGAGGTPG------------------------------------------------------------GPGGGGAPPRYATLEHPFHC
HFZ3   LVDLNLAG-------EPTEGAPV----------------------------------------------------------------------------AVQRDYG--------FWC
HFZ4   CMEGPGD--------EE--------------------------------------------------------------------------------VPLPHKTPI--------QP
HFZ5   CMDYNRSEATTAPPRPFPAKPTLPG---------------------------------------------------PPGA----------PASGG-----ECPAGGPFV-----CKC
HFZ6   TFDPHTEF-------LGPQKKTE------------------------------------------------------------------------------QVQRDIG-------FWC
HFZ7   VGQNTSDGSGPGGGPTAYPLPDLPFTALPPG----------------------------------------------------------------ASDGRGRPAF-----PFSC
HFZ8   CMDYNRTDLTTAAPSPPRRLPPPPP-GEQPPSGSGHGRPPGARPPHPGGGRGGGGGDAAAPPARGGGGGGKARPPGGGAAP---CEPGCQC
HFZ9   CMEAPENA-TAGPAEPHKGLGMLPV---------------------------------------------------------------------APRPARPPG-------DLGP
HFZ10  NYLCMEAPNN----GSDEPTRGSGLFPP-----------------------------------------------------------------LFRPQRPHSAQ----EHP
```

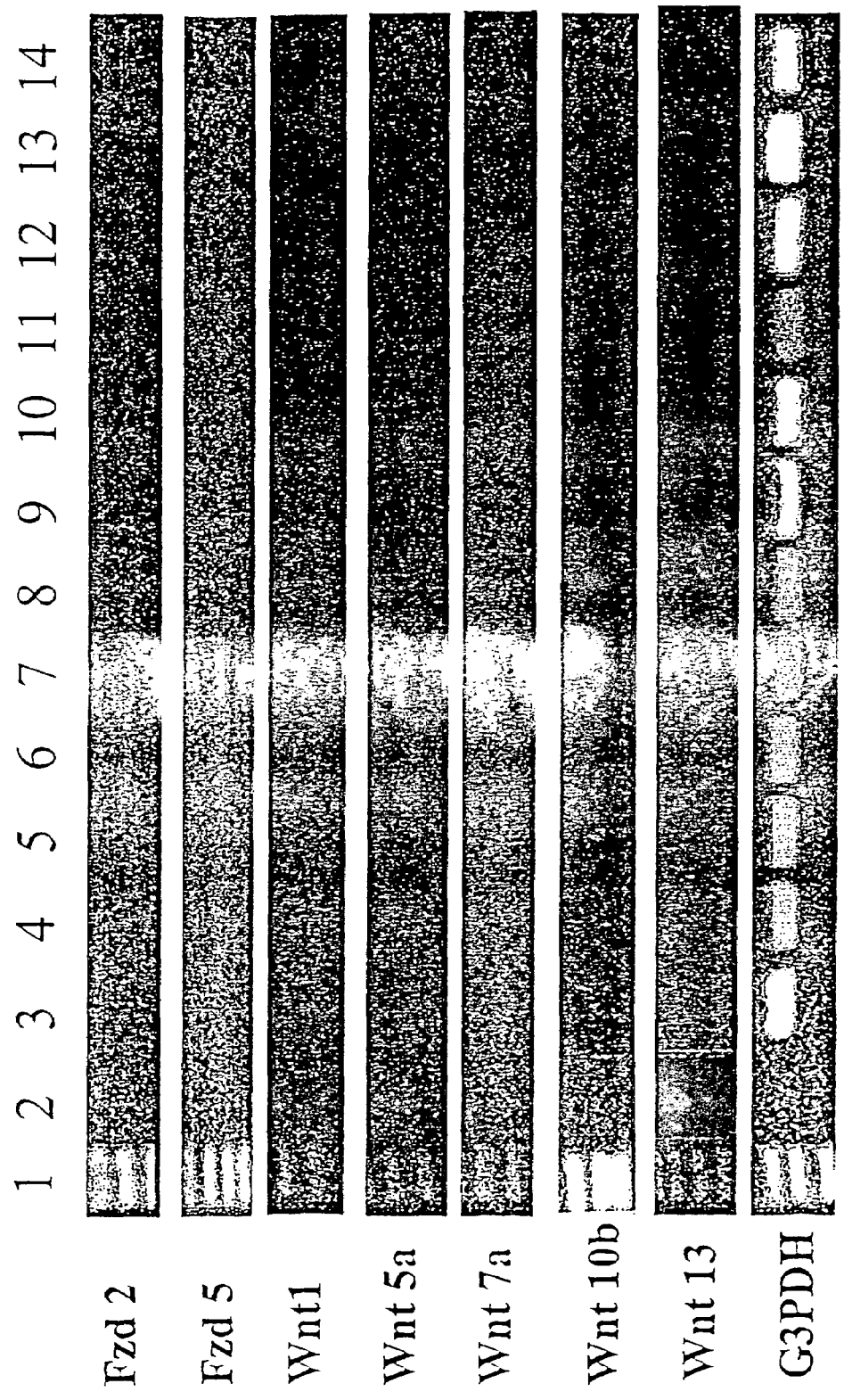

US 7,682,607 B2

WNT AND FRIZZLED RECEPTORS AS TARGETS FOR IMMUNOTHERAPY IN HEAD AND NECK SQUAMOUS CELL CARCINOMAS

CROSS-REFERENCE TO RELATED APPLICATIONS

This patent application claims the benefit of the filing date of U.S. Provisional Application No. 60/287,995, filed 1 May 2001 which is incorporated herein by reference.

STATEMENT OF RIGHTS TO INVENTIONS MADE UNDER FEDERALLY SPONSORED RESEARCH

This invention was made with U.S. Government support under Grant AR 44850 awarded by the National Institutes of Health. The Government may have certain rights in this invention.

TECHNICAL FIELD

This application relates to proteins involved in the Wnt/frizzled signaling pathway. More specifically, it involves the role of these proteins in proliferative disorders.

BACKGROUND OF THE INVENTION

Many cancers arise from differentiated tissues that are slowly dividing. The initial malignant population may have developed from a small, rapidly proliferating population of residual tissue stem cells or cells with a less differentiated subcellular profile. A strategy for targeting tumor cells that are antigenically distinct from mature differentiated cells could be useful in the treatment of cancer, particularly for controlling microscopic spread of disease. Malignant cells may express receptors used in embryonic patterning, which may serve as immunologic targets distinct from mature differentiated tissue.

In embryogenesis body patterning is related to the axial expression of different proteins. The proximal-distal axis is controlled by fibroblast growth factor (Vogel, A. et al., "Involvement of FGF-8 in initiation, outgrowth and patterning of the vertebrate limb," *Development* 122:1737-1750 (1996); Vogel, A. and Tickle, C., "FGF-4 maintains polarizing activity of posterior limb bud cells in vivo and in vitro," *Development* 119:199-206 (1993); Niswander, L. et al., "FGF-4 replaces the apical ectodermal ridge and directs outgrowth and patterning of the limb," *Cell* 75:579-587 (1993)), anterior-posterior axis by Sonic hedgehog (Riddle, R. D. et al., "Sonic hedgehog mediates the polarizing activity of the ZPA," *Cell* 75:1401-1416 (1993)), and the dorsal ventral axis by wingless (Parr, B. A. et al., "Mouse Wnt genes exhibit discrete domains of expression in the early embryonic CNS and limb buds," *Development* 119:247-261 (1993); Riddle, R. D. et al., "Induction of the LIM homeobox gene Lmx1 by Wnt7a establishes dorsoventral pattern in the vertebrate limb," *Cell* 83:631-640 (1995); Vogel, A. et al., "Dorsal cell fate specified by chick Lmx1 during vertebrate limb development," *Nature* 378:716-720 (1995)). These factors are closely cross-regulated in development. The secretion of Wnt (wingless) is stimulated by Sonic hedgehog (SHH) signaling and conversely the expression of SHH is supported by the continued presence of wingless. SHH in turn influences fibroblast growth factor (FGF) expression (Niswander, L. et al., "A positive feedback loop coordinates growth and patterning in the vertebrate limb," *Nature* 371:609-612 (1994); Niswander, L., et al. "Function of FGF-4 in limb development," *Mol Reprod Dev* 39:83-88; discussion 88-89 (1994); Laufer, E. et al., "Sonic hedgehog and Fgf-4 act through a signaling cascade and feedback loop to integrate growth and patterning of the developing limb bud," *Cell* 79:993-1003 (1994)). Wingless is a ligand for a G-coupled protein receptor named frizzled, which mediates a complex signaling cascade (Vinson, C. R. and Adler, P. N., "Directional non-cell autonomy and the transmission of polarity information by the frizzled gene of Drosophila," *Nature* 329:549-551 (1987)). Transcriptional regulation is also mediated by SHH cell surface interaction with its ligand, Patched. Patched tonically inhibits signaling through Smoothened until it binds to SHH. These pathways are illustrated in FIG. 1, which has been adapted from reviews by others (Hunter, T., "Oncoprotein networks," *Cell* 88:333-346 (1997); Ng, J. K. et al., "Molecular and cellular basis of pattern formation during vertebrate limb development," *Curr Top Dev Biol* 41:37-66 (1999); Ramsdell, A. F. and Yost, H. J., "Molecular mechanisms of vertebrate left-right development," *Trends Genet.* 14:459-465 (1998)).

Head and neck squamous cell carcinoma (HNSCC) is the sixth most common cancer in developed countries, and of the 44,000 annual cases reported in the United States approximately 11,000 will result in an unfavorable outcome (Landis, S. H. et al., "Cancer statistics," *CA Cancer J Clin.* 49, 8-31 (1999); Parkin, D. M. et al., "Global cancer statistics," *CA Cancer J Clin.* 49, 33-64 (1999)). Although metastatic HNSCC can respond to chemotherapy and radiotherapy, it is seldom adequately controlled. Therefore, it is important to identify new molecular determinants on HNSCC that may be potential targets for chemotherapy or immunotherapy.

In APC-deficient colon carcinoma, beta-catenin accumulates and is constitutively complexed with nuclear Tcf-4 (Sparks, A. B. et al., "Mutational analysis of the APC/beta-catenin/Tcf pathway in colorectal cancer," *Cancer Res* 58:1130-1134 (1998)). Other colon carcinomas and melanomas also contain constitutive nuclear Tcf-4/beta-catenin complexes as a result of mutations in the N terminus of beta-catenin that render it insensitive to downregulation by APC, and GSK3 beta (Morin, P. J. et al., "Activation of beta-catenin-Tcf signaling in colon cancer by mutations in beta-catenin or APC," *Science* 275:1787-1790 (1997); Rubinfeld, B. et al. "Stabilization of beta-catenin by genetic defects in melanoma cell lines," *Science* 275:1790-1792 (1997)). This results in the unregulated expression of Tcf-4 oncogenic target genes, such as c-myc, cyclin D1, and c-jun (He, T. C. et al., "Identification of c-MYC as a target of the APC pathway," *Science* 281:1509-1512 (1998); Shtutman, M. et al., "The cyclin D1 gene is a target of the beta-catenin/LEF-1 pathway," *Proc. Nat'l. Acad. Sci. USA* 96:5522-5527 (1999); Li, L. et al., "Disheveled proteins lead to two signaling pathways. Regulation of LEF-1 and c-Jun N-terminal kinase in mammalian cells," *J Biol Chem* 274:129-134 (1999)). The expression of covalently linked beta-catenin and LEF-1. has been directly demonstrated to result in the oncogenic transformation of chicken fibroblasts (Aoki, M. et al., "Nuclear endpoint of Wnt signaling: neoplastic transformation induced by transactivating lymphoid-enhancing factor 1," *Proc. Nat'l. Acad. Sci. USA* 96:139-144 (1999)). Similar mechanisms leading to deregulation of Tcf target gene activity are likely to be involved in melanoma (Rimm, D. L. et al., "Frequent nuclear/cytoplasmic localization of beta-catenin without exon 3 mutations in malignant melanoma," *Am J Pathol* 154:325-329 (1999)), breast cancer (Bui, T. D. et al., "A novel human Wnt gene, WNT10B, maps to 12q13 and is expressed in human breast carcinomas," *Oncogene* 14:1249-1253 (1997)), heptocellular carcinoma (de La Coste, A. et al., "Somatic mutations of the beta-catenin gene are frequent in mouse and human heptocellular carcinomas," *Proc Nat'l. Acad. Sci. USA* 95:8847-8851 (1998)), ovarian cancer (Palacios, J., and Gamallo, C., "Mutations in the beta-catenin gene (CTNNB1) in endometrioid ovarian carcinomas," *Cancer Res* 58:1344-1347 (1998)), endometrial cancer (Ikeda, T., "Mutational analysis of the CTNNB1 (beta-catenin) gene in human endometrial cancer: frequent mutations at codon 34 that cause nuclear accumulation," *Oncol Rep* 7:323-326 (2000)), medulloblastoma (Hamilton, S. R. et al., "The molecular basis of Turcot's syndrome," *N. Engl J Med* 332:839-847 (1995)), pilomatricomas (Chan, E. F. et al. "A common human skin tumour is caused by activating mutations in beta-catenin," *Nat. Genet.* 21:410-413 (1999)), and prostate cancer (Iozzo, R. V. et al., "Aberrant expression of the growth factor Wnt-5A in human malignancy," *Cancer Res* 55:3495-3499 (1995)).

Other growth regulation pathways in tumors have also attracted recent interest. Many epithelial tumors express excess amounts of epidermal growth factor-receptor tyrosine kinases, particularly epidermal growth factor receptor (EGFR, or ErbB-1), and HER2 (ErbB-2) (Coussens, L. et al., "Tyrosine kinase receptor with extensive homology to EGF receptor shares chromosomal location with neu oncogene," *Science* 230:1132-1139 (1985); King, C. R. et al., "Amplification of a novel v-erbB-related gene in a human mammary carcinoma," *Science* 229:974-976 (1985)). HER2 is transmembrane tyrosine kinase receptor, which dimerizes with another member of the EGFR family to form an active dimeric receptor (Akiyama, T. et al., "The product of the human c-erbB-2 gene: a 185-kilodalton glycoprotein with tyrosine kinase activity," *Science* 232:1644-1646 (1986)). The resulting phosphorylation of tyrosine residues initiates complex signaling pathways that ultimately lead to cell division. HER2 is overexpressed in 25 to 30 percent of breast cancers, usually as a result of gene amplification (Slamon, D. J. et al., "Studies of the HER-2/neu proto-oncogene in human breast and ovarian cancer," *Science* 244:707-712 (1989)). High levels of this protein is associated with an adverse prognosis (Slamon, D. J. et al., "Human breast cancer: correlation of relapse and survival with amplification of the HER-2/neu oncogene," *Science* 235:177-182 (1987); Ravdin, P. M. and Chamness, G. C., "The c-erbB-2 proto-oncogene as a prognostic and predictive marker in breast cancer: a paradigm for the development of other macromolecular markers—a review," *Gene* 159:19-27 (1995)).

In the past decade there has been tremendous progress in identifying genetic and molecular changes that occur during the transformation of malignant cells. Many malignant cells have a less differentiated phenotype, and a higher growth fraction than normal in adult tissues. These basic characteristics are similar to immature or embryonic cells. During the development of the embryo, various cell surface receptors and ligands direct tissue pattern formation, and cellular differentiation (Hunter, T., "Oncoprotein networks," *Cell* 88, 333-346 (1997); Ng, J. K. et al., "Molecular and cellular basis of pattern formation during vertebrate limb development, "*Curr Top Dev Biol.* 41, 37-66 (1999); Ramsdell, A. F. and Yost, H. J., "Molecular mechanisms of vertebrate left-right development," *Trends Genet.* 14, 459-465 (1998)). The expression of these receptors and ligands is often no longer required in fully matured adult tissues. Because they are expressed on the cell surface, the receptors and ligands important for morphologic patterning and tissue differentiation could be targets for the immunotherapy of tumors that have arisen from residual immature cells, or that have undergone de-differentiation.

Genes of the wingless (Wnt) and frizzled (Fzd) class have an established role in cell morphogenesis and cellular differentiation (Parr, B. A. et al., "Mouse Wnt genes exhibit discrete domains of expression in the early embryonic CNS and limb buds," *Development,* 119, 247-261 (1993); Riddle, R. D. et al., "Induction of the LIM homeobox gene Lmx1 by WNT7a establishes dorsoventral pattern in the vertebrate limb," *Cell* 83, 631-640 (1995); Vogel, A. et al., (1995) "Dorsal cell fate specified by chick Lmx1 during vertebrate limb development," *Nature* 378, 716-720 (1995)). The Wnt proteins are extracellular ligands for the Fzd receptors, which resemble typical G protein coupled receptors (GPCRs). The first member of the 19 known human Wnt genes, Wnt-1, was initially discovered because of its oncogenic properties (Nusse, R. and Varmus, H. E., "Many tumors induced by the mouse mammary tumor virus contain a provirus integrated in the same region of the host genome," *Cell* 31, 99-109 (1982)). The Wnt glycoproteins bind to one or more of the 9 known, 7 transmembrane domain G-protein coupled Fzd receptors, to initiate a chain of signaling events that often culminates in the stabilization and nuclear translocation of β-catenin, with resultant heterodimerization with one of the four members of the LEF/TCF family of transcription factors (Cadigan, K. M. and Nusse, R., "Wnt signaling: a common theme in animal development," *Genes Dev.,* 11, 3286-3305 (1997); Miller, J. R. et al., "Mechanism and function of signal transduction by the Wnt/β-catenin and Wnt/Ca2+ pathways," *Oncogene* 18, 7860-7872 (1999)). These transcription factor complexes control the activities of specific Wnt target genes, including developmental regulators and other genes involved in coordinating cell proliferation, cell-cell interactions, and cell-matrix interactions (Vogel, A. and Tickle, C., "FGF-4 maintains polarizing activity of posterior limb bud cells in vivo and in vitro," *Development* 119:199-206 (1993)). The overexpression of β-catenin and LEF-1 has been demonstrated to result in the oncogenic transformation of chicken fibroblasts (Aoki, M. et al., "Nuclear endpoint of Wnt signaling: neoplastic transformation induced by transactivating lymphoid-enhancing factor 1," *Proc. Nat'l. Acad. Sci. USA* 96, 139-144 (1999)).

A recent survey using microarray techniques showed that most HNSCC overexpress mRNAs of the Wnt family (Leethanakul, C. et al., "Distinct pattern of expression of differentiation and growth-related genes in squamous cell carcinomas of the head and neck revealed by the use of laser capture microdissection and cDNA arrays," *Oncogene* 19, 3220-3224 (2000)). However, the various Wnt mRNAs are very homologous, and hybridization in microarrays often cannot distinguish between closely related templates.

A murine monoclonal antibody 4DS binds with high affinity to the extracellular domain of HER2, thereby blocking its function in signal transduction (Hudziak, R. M. et al. "p185HER2 monoclonal antibody has antiproliferative effects in vitro and sensitizes human breast tumor cells to tumor necrosis factor," *Mol Cell Biol* 9:1165-1172 (1989); Fendly, B. M. et al. "Characterization of murine monoclonal antibodies reactive to either the human epidermal growth factor receptor or HER2/neu gene product," *Cancer Res* 50:1550-1558 (1990); Fendly, B. M. et al. "The extracellular domain of HER2/neu is a potential immunogen for active specific immunotherapy of breast cancer," *J Biol Response Mod* 9:449-455 (1990)). In experimental models of breast cancer, it was active in vitro and in vivo, and had greater anti-tumor effects when combined with chemotherapy Hudziak, R. M. et al. "p185HER2 monoclonal antibody has antiproliferative effects in vitro and sensitizes human breast tumor cells to tumor necrosis factor," *Mol Cell Biol* 9:1165-1172 (1989); Pietras, R. J. et al., "Antibody to HER-2/neu receptor blocks DNA repair after cisplatin in human breast and ovarian cancer cells," *Oncogene* 9:1829-1838 (1994). A recently completed phase 3 randomized clinical trial of a humanized form of 4DS monoclonal antibody, trastuzumab (Herceptin; Genentech, Inc, South San Francisco, Calif.), demonstrated efficacy against some forms of breast tumors overexpressing HER2 (Slamon, D. J. et al., "Use of chemotherapy plus a monoclonal antibody against HER2 for metastatic breast cancer that overexpresses HER2," *N Engl J Med* 344:783-792 (2001).

SUMMARY OF THE INVENTION

A method for determining overexpression of a wnt or frizzled gene in a tumor cell comprising:

(a) isolating messenger RNA from a tumor cell and from a corresponding normal cell from the same source;

(b) performing reverse transcription PCR on the tumor cell and the normal cell utilizing primers directed against regions of the wnt or frizzled gene that are non-homologous with a known wnt gene or a known frizzled gene and obtaining amplicons from the reverse transcription PCR;

(c) assessing the concentrations of the resulting amplicons of step (b) in comparison to a control housekeeping gene; and (d) identifying tumor cells that overexpress a wnt or frizzled gene at about five fold compared to normal cells tissue from the same source An isolated antibody directed against at least one sequence that corresponds to a non-homologous regions of a known wnt gene or a known frizzled gene.

A method of detecting overexpression of at least one wnt and/or frizzled protein in a cancer cell compared to a non-cancer cell comprising:

(a) contacting the cancer cell with an antibody directed against at least one sequence that corresponds to a non-homologous region of a known wnt or a known frizzled gene;

(b) contacting the non-cancer cell with the same antibody as in step (a);

(c) comparing the interaction of the antibody with the cancer cell to the interaction of the antibody with the non-cancer cell; and (d) correlating the interactions in (c) with the expression levels of the wnt and/or frizzled protein in both the cancer cell and the non-cancer cell.

A method for altering the growth of a cell overexpressing at least one wnt and/or frizzled protein comprising:

contacting the cell with a non-crossreactive antibody against the wnt and/or frizzled protein.

A method for altering the growth of a cell overexpressing at least one wnt and/or frizzled protein comprising:

contacting the cell with a synthetic peptide, a recombinant protein, or a DNA vector, or any combination of a synthetic peptide and a recombinant protein and a DNA vector, comprising at least one non-homologous region of known wnt and/or frizzled proteins.

BRIEF DESCRIPTION OF THE DRAWINGS

FIGS. 4A, 4B, and 4C. An inhibition of proliferation assay in a HNSCC line is depicted. Specifically, anti-frizzled 2, anti-wnt 1, and anti-wnt 10b are tested for their ability to inhibit proliferation.

FIG. 6. Sequence alignment of a portion of the first extracellular region of human Frizzled receptors is depicted.

FIG. 7A depicts an immunoblot after treatment with Wnt 1 or Wnt 10b antibodies. SNU1076 cells were treated for 72 hrs with 2 µg/ml of anti-Wnt 1, Wnt 10b, or control antibodies. FIG. 7B shows that treatment with Wnt 1 antibodies reduces transcription of TCF/LEF gene.

FIGS. 8A and 8B. FIG. 8A depicts an RT-PCR amplification for Wnt/FZD families in cancer cell lines. FIG. 8B depicts an RT-PCR amplification for Wnt/FZD families in normal cells.

DETAILED DESCRIPTION OF THE DRAWINGS

Figure 1:
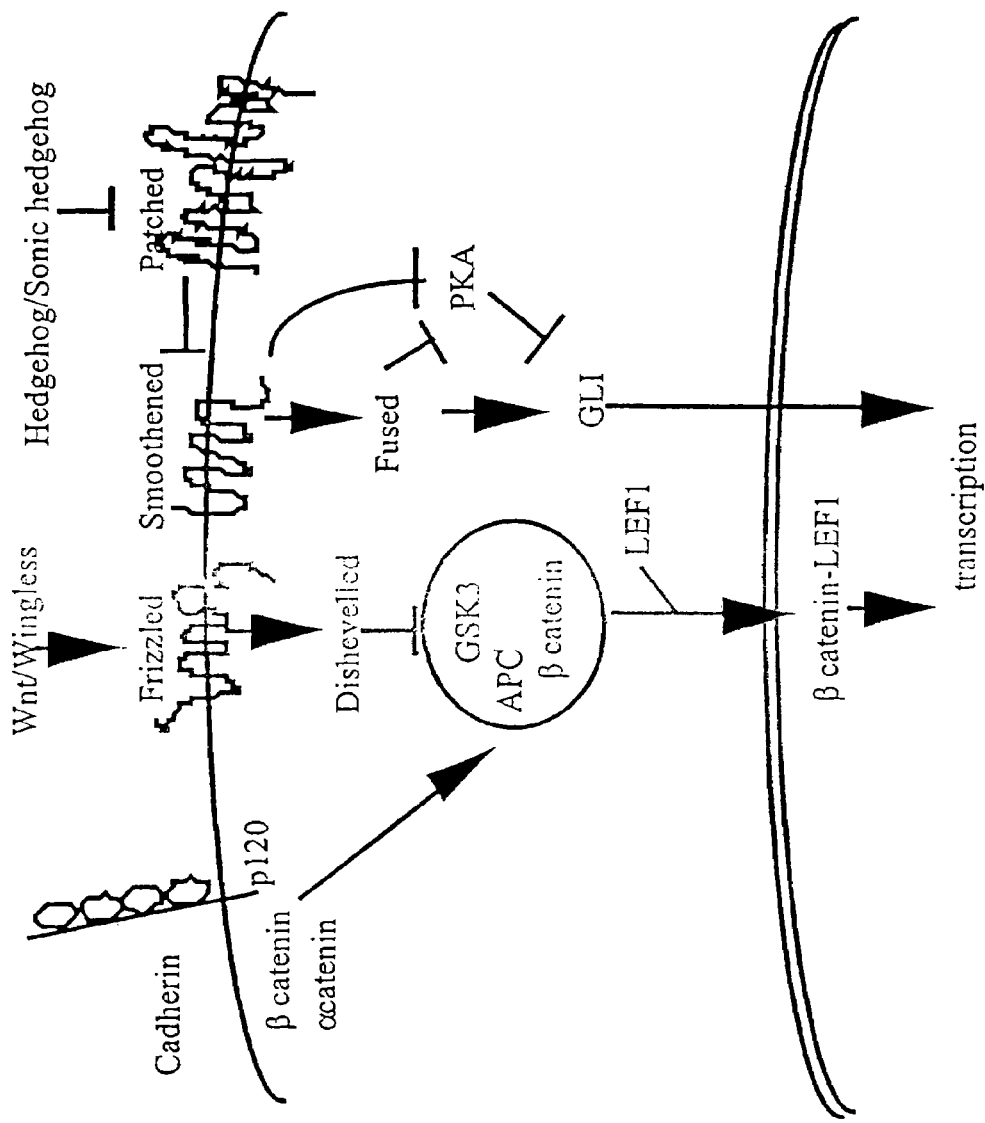
FIG. 1. Several developmental signaling pathways are depicted.

FIG. 1. Schematic of developmental signaling pathways is depicted. The signalling pathways of the Wnt/wingless and Hedehog/Sonic hedgehog are shown. Both sets of ligands interact with a cell surface receptor. Proteins involved in the signalling pathway are shown, for example, LEF1 and GS $K_3$.

Figure 2:
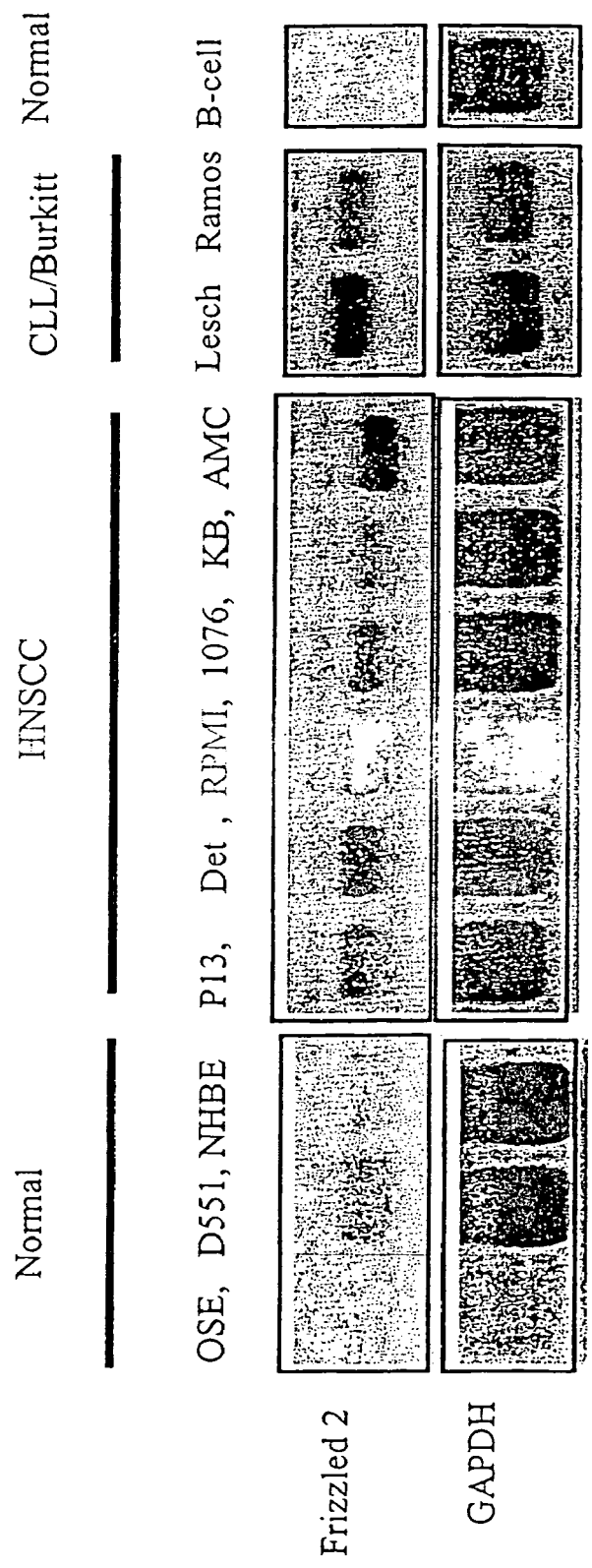
FIG. 2. RT-PCR analysis of a subset of HNSCC and B-cell lines for frizzled 2 mRNA.

FIG. 2. RT-PCR analysis of a subset of HNSCC and B-cell lines for frizzled 2 mRNA. Total RNA was extracted from HNSCC lines (PCI13, Detroit 562, RPMI 2650, SNU 1076, KB, AMC4), a CLL line (Lesch), a Burkitt lymphoma line (Ramos), glioma lines (U87MG, and U373MG), normal human bronchial epithelial cell lines (Clonetics, San Diego, Calif.) and normal oral squamous epithelial (OSE) cells using RNAzol (Gibco BRL, Grand Island, N.Y.). Reverse transcription was performed using 1 µg of RNA from each sample and the Superscript™ Preamplification kit (Gibco BRL). Frizzled 2 was amplified with 25 cycles of PCR. G3PDH mRNA was amplified in a separate reaction for each sample.

Figure 3:
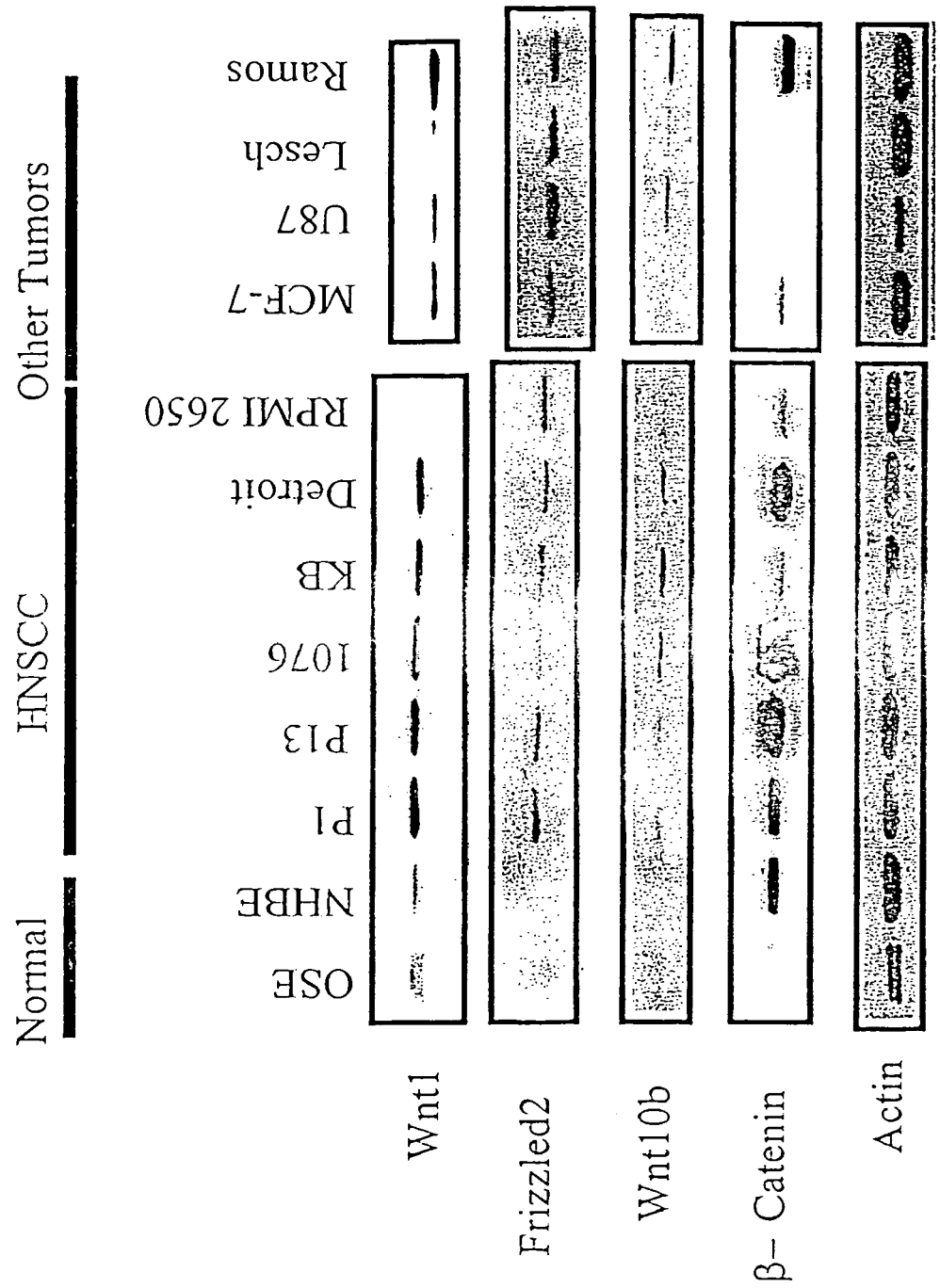
FIG. 3. A western blot analysis of tumor and normal cells for frizzled 2, wnt1 and 10b.

FIG. 3. A sample western blot analysis of tumor and normal cells for frizzled 2, wnt 5A and 10b. Adherent cells in culture were harvested and lysed with a solution containing 25 mM Tris HCl, 150 mM KCl, 5 mM EDTA, 1% NP-40, 0.5% sodium deoxycholic acid, 0.1% sodium dodecyl sulfate, 1 mM NaVO$_3$, 1 mM NaF, 20 mM (β-glycerophosphate and protease inhibitors. Twenty µg of protein from each cell line was separated by SDS-PAGE and transferred to a PVDF membrane. The membrane was immersed in 2% I-block, 0.05% Tween X in PBS and then incubated with a 1:500 dilution of polyclonal goat anti-human Wnt 1, Wnt 10b, or frizzled 2 IgG (Santa Cruz Biotechnology, Santa Cruz, Calif.). These primary antibodies were then detected by horseradish peroxidase-conjugated donkey anti-goat IgG (Santa Cruz) and chemiluminescence (ECL detection reagents, Amersham Life Science, Aylesbury, UK). To verify relative amount of protein transferred in each lane, the presence of actin was measured with an actin monoclonal antibody (Chemi-Con International Inc, Temecula, Calif.).

Figure 4A:
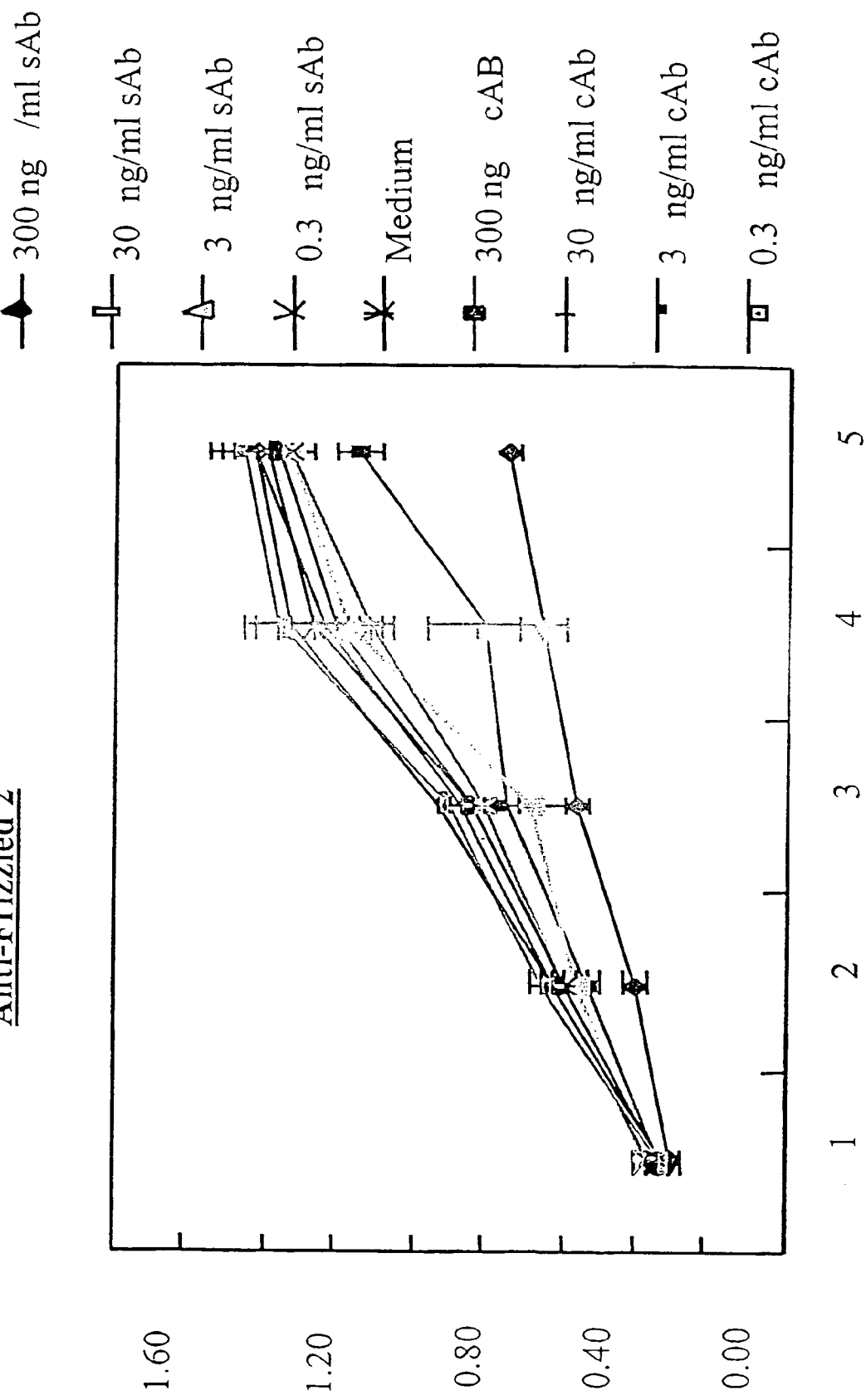
Figure 4C:
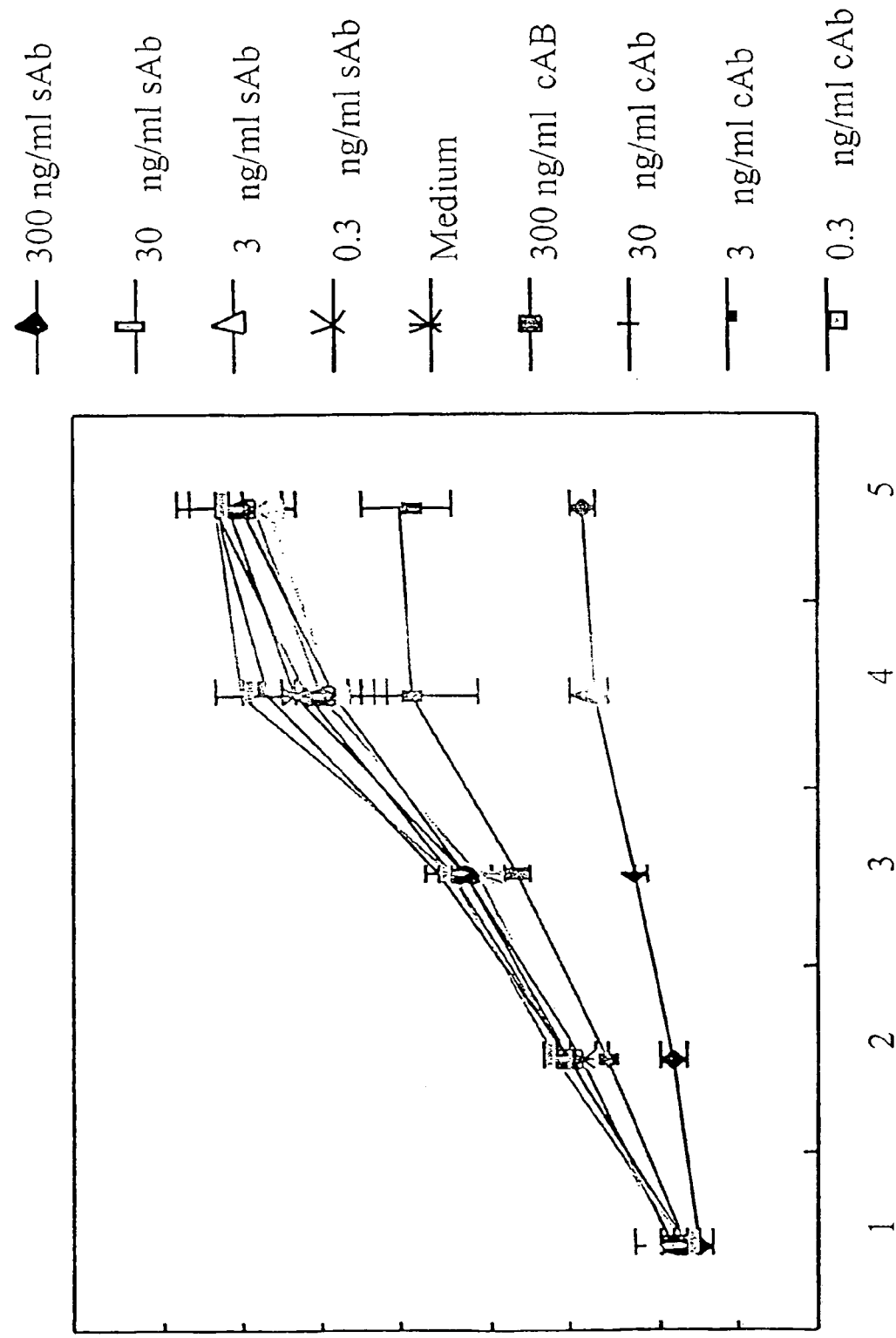

FIGS. 4A, 4B, and 4C. Inhibition of proliferation in a HNSCC line. Briefly, either $7.5 \times 10^3$ or $10 \times 10^3$ SNU1076 cells per well were seeded in 96 well plates. After 24 hours, graded amounts of polyclonal goat anti-human frizzled 2, Wnt 1, or Wnt 10b IgG (sAB)(Santa Cruz Biotechnology, Santa Cruz, Calif.), or control goat anti-human IgG. (cAB) (Fisher Scientific, Pittsburgh, Pa.) were added. On days 1, 2, 3, or 4, 20 µl of MTT (3-[4,5-dimethylthiazol-2-yl]-2,5-diphenyl tetrazolium bromide)-based solution was added to wells for four hours prior to lysis with 15% SDS, 0.015 M HCl. Absorbencies of 570 and 650 nm were measured.

Figure 5:
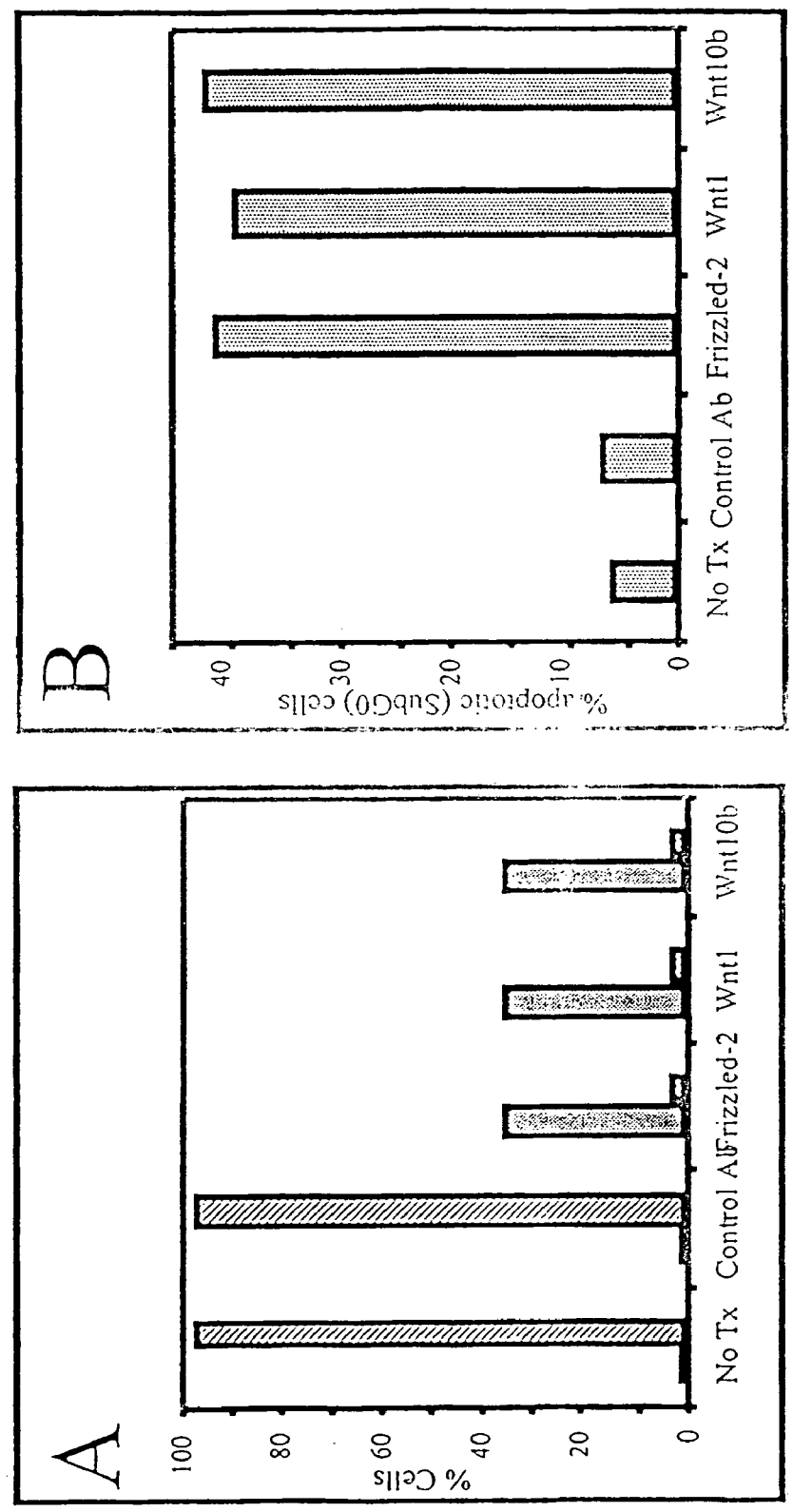
FIG. 5. Apoptotic effects of inhibition of the Wnt/Frizzled signaling pathway in a HNSCC line is depicted.

FIG. 5. Apoptotic effect of inhibition of the Wnt/Frizzled signaling pathway in a HNSCC line. The HNSCC line SNU1076, growing in RPMI-1640 supplemented with 10% FBS, was treated for 72 hrs with 300 ng/ml anti-Frizzled 2, Wnt-1, Wnt10b, or control nonspecific polyclonal antibodies. The cytotoxic effects of these antibodies were assessed by vital dye retention and DNA content. Panel A: cells were detached from the flasks by trypsin treatment and incubated for 10 minutes in growing medium with 5 µg/ml Propidium iodide (PI) and 40 nM $DiOC_6$ and analyzed by flow cytometry. Viable cells (stripes) had high $DiOC_6$ (FL-1) and low PI (FL-3) fluorescence, and apoptotic cells (stippled) had low $DiOC_6$ (FL-1) and low PI (FL-3) fluorescence. Panel B: cells were detached from the flasks by trypsin treatment and incubated overnight in a hypotonic buffer (0.1% citrate, 0.1% SDS) containing 50 µg/ml PI and 100 µg/ml RNase. The amount of DNA was then measured by flow cytometry, and apoptotic cells were defined as having a DNA content lower than the $G_0G_1$ levels (sub-$G_0$ cells).

FIG. 6. Sequence alignment of a portion of the first extracellular region of human Frizzled receptors. Specifically, the amino acid sequences of HFZ1 through HFZ10 are aligned to show similarity.

Figure 7A:
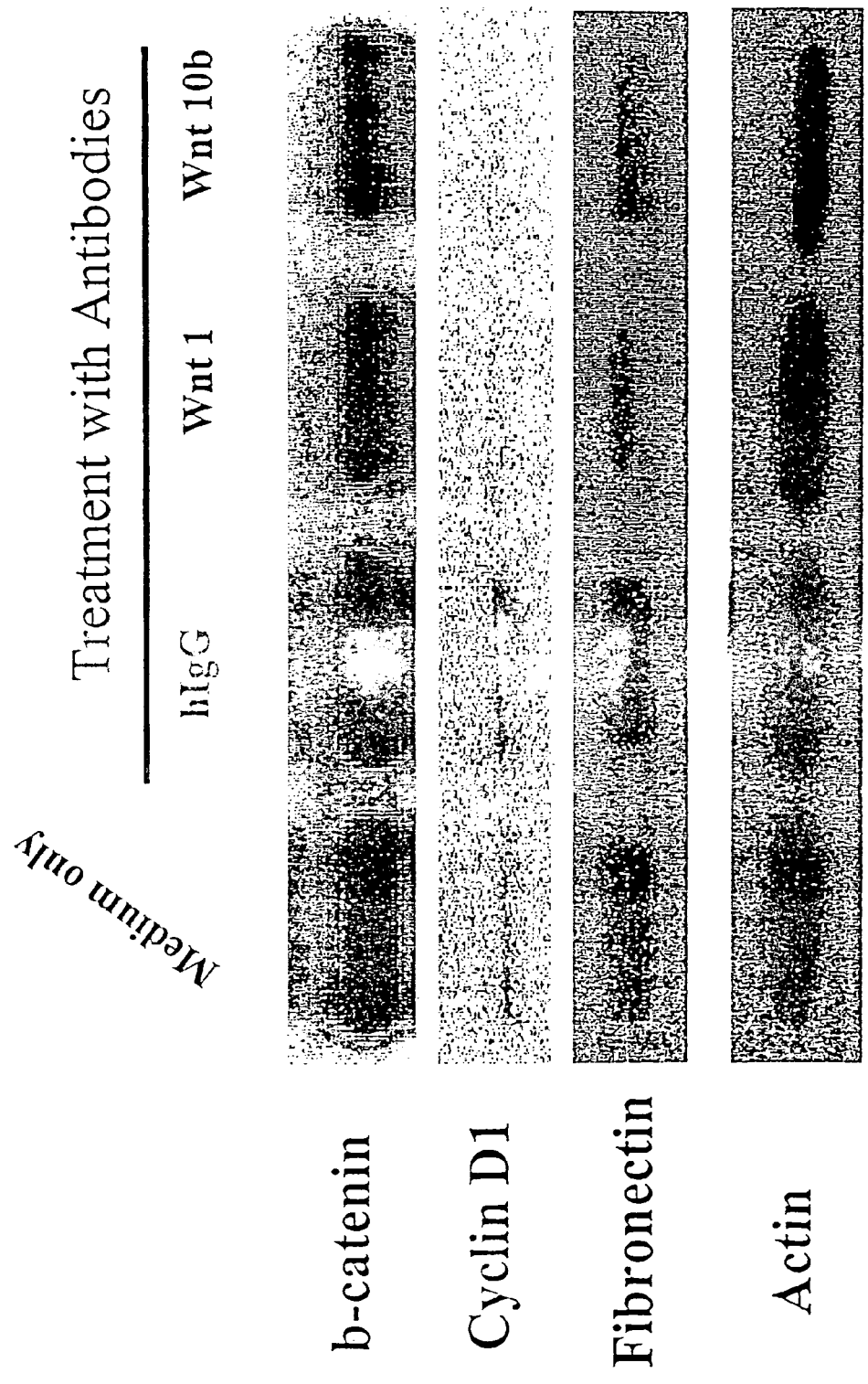
FIGS. 7A and 7B.
Figure 7B:
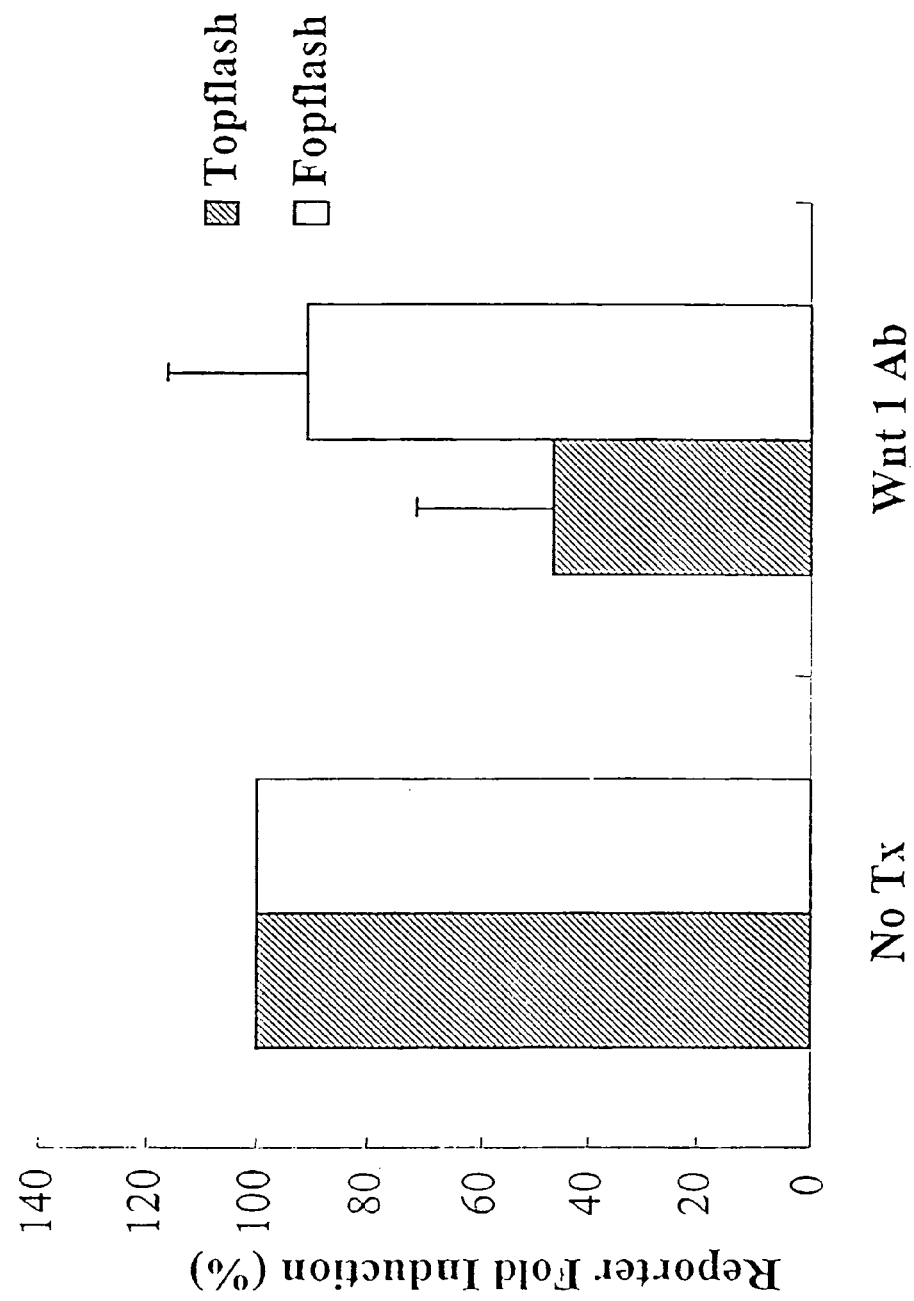

FIGS. 7A and 7B. FIG. 7A: immunoblot after treatment with Wnt 1 or Wnt 10b antibodies. SNU1076 cells were treated for 72 hrs with 2 µg/ml of anti-Wnt 1, Wnt 10b, or control antibodies. Twenty µg of protein from each cell line was separated by SDS-PAGE and transferred to a PVDF membrane. The membrane was immersed in 2% I-block, 0.05% Tween X in PBS and then incubated with a monoclonal anti-human β-catenin, cyclin D1, or fibronectin IgG. These primary antibodies were then detected by horseradish peroxidase-conjugated anti-IgG and chemiluminescence. To verify and compare relative amounts of protein in each lane, PVDF membrane was stripped with Re-Blot™ Western blot recycling kit and reprobed for other antibodies or actin monoclonal antibody. FIG. 7B: treatment with Wnt1 antibodies reduces transcription of TCF/LEF gene. SNU 1076 cells were treated with 2 µg/ml of anti-Wnt-1, or control antibodies for 36 hrs. SNU 1076 cells were cotransfected with 0.5 µg/ml of pTOPFLASH-Luc or pFOPFLASH-Luc and 0.5 µg/ml of pCMV-PGa1. Cells were harvested 24 h after transfection, and lysed in lysis buffer. Luciferase and (3-galactosidase activities determined using Dual-Light™ reporter gene assay system. Luciferase activities of each of pTOPFLASH-Luc or pFOPFLASH-Luc and (3-galactosidase activities of pCMV-βGal were measured in the same sample by luminometer. Transfection efficiency of each sample was normalized by the activity of β-galactosidase activity.

Figure 8A:
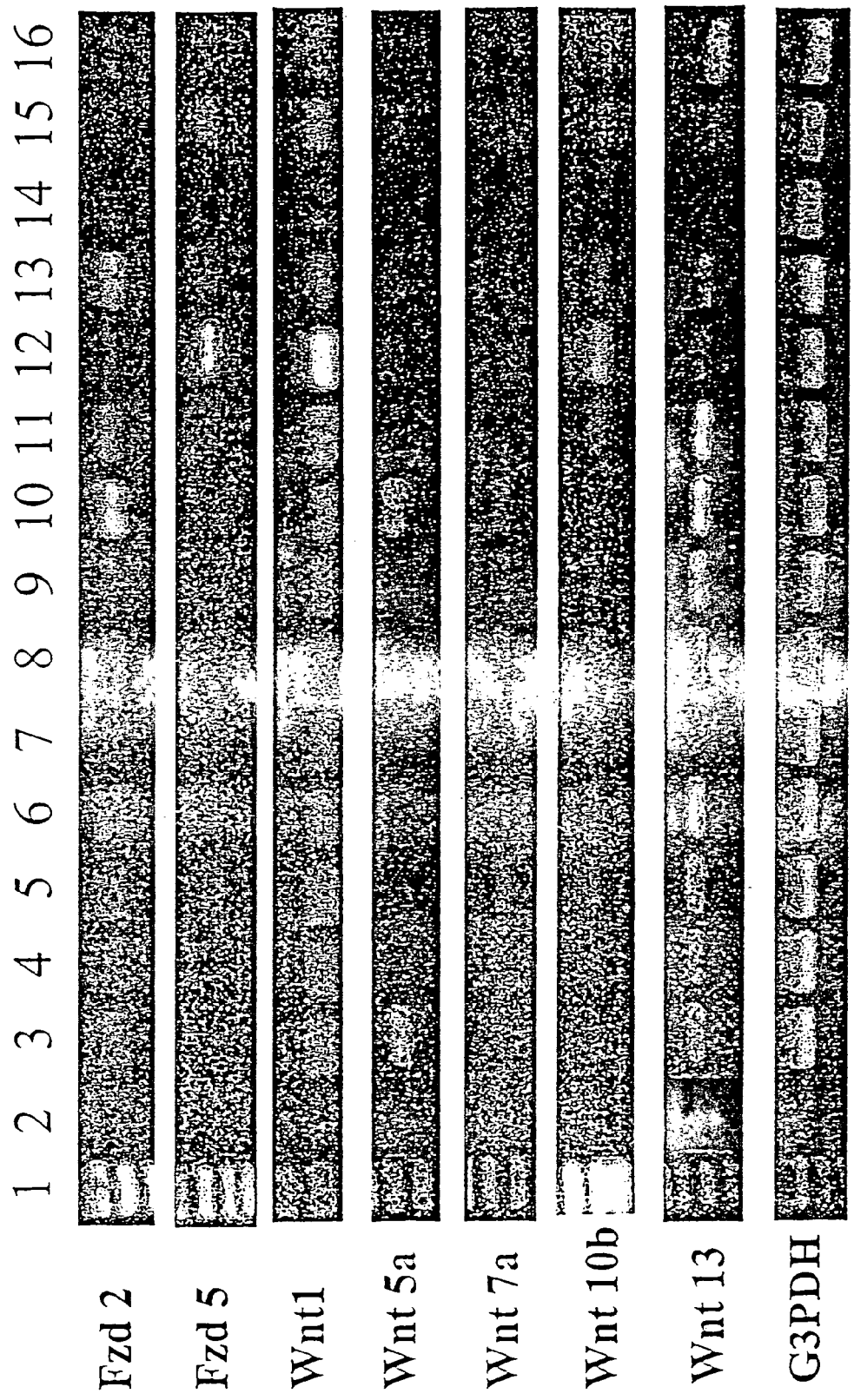

FIGS. 8A and 8B. FIG. 8A: RT-PCR amplification for Wnt/FZD families in cancer cell lines. Lane 1: DNA standard, lane 2: $H_2O$, Lanes 3 and 4: glioblastoma, lanes 5-14: head and neck cancers, lanes 15 and 16: B cell cancers. FIG. 8B: RT-PCR amplification for Wnt/FZD families in normal cells. Lane 1: DNA standard, lane 2: $H_2O$, lanes 7 and 14: normal human bronchial epithelial cell, other lanes: normal oral squmous cells.

Figure 9A:
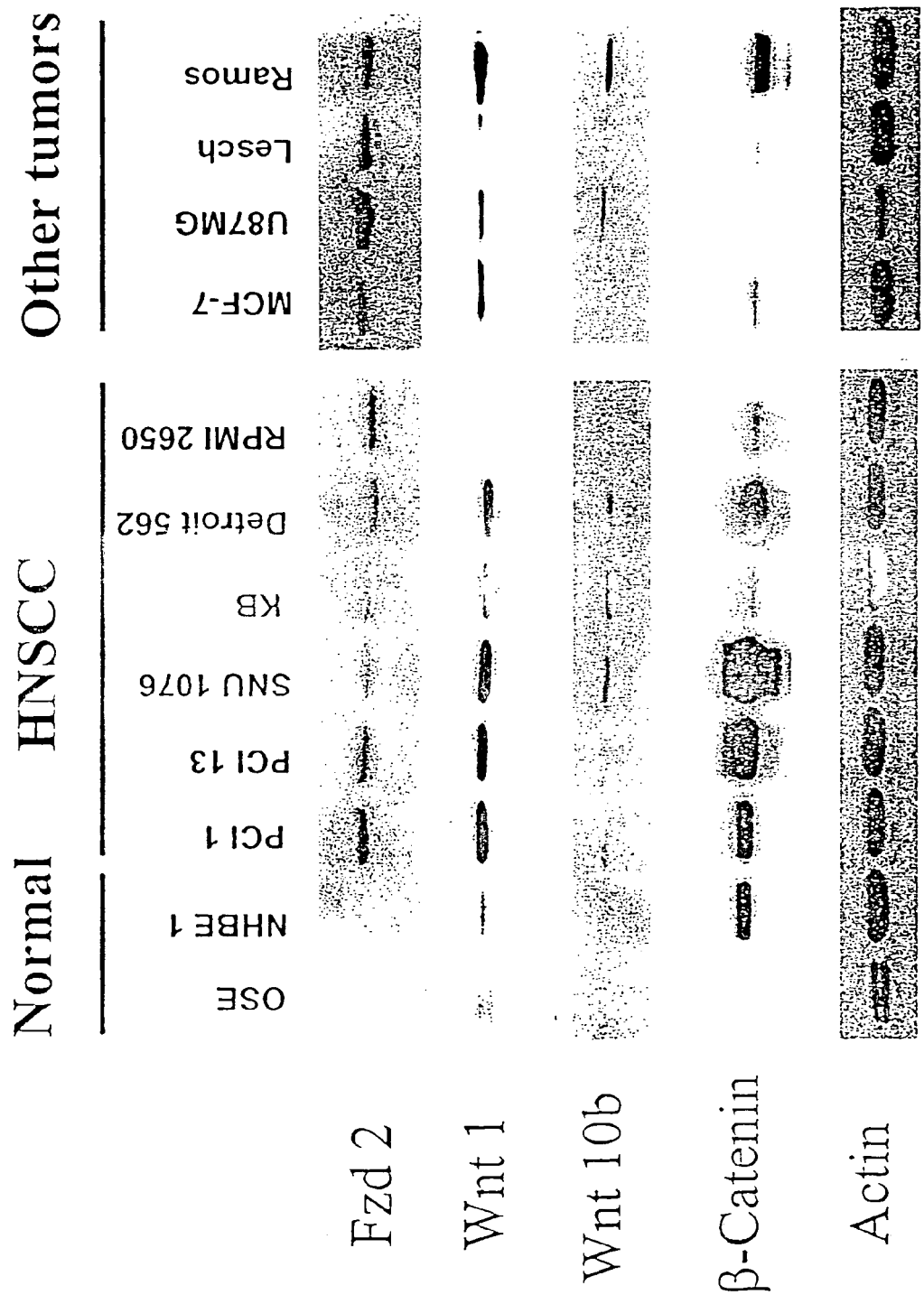
FIGS. 9A and 9B. Protein expression of FZD 2, Wnt 1, Wnt 10b, β-catenin and actin in normal and malignant cells.
Figure 9B:
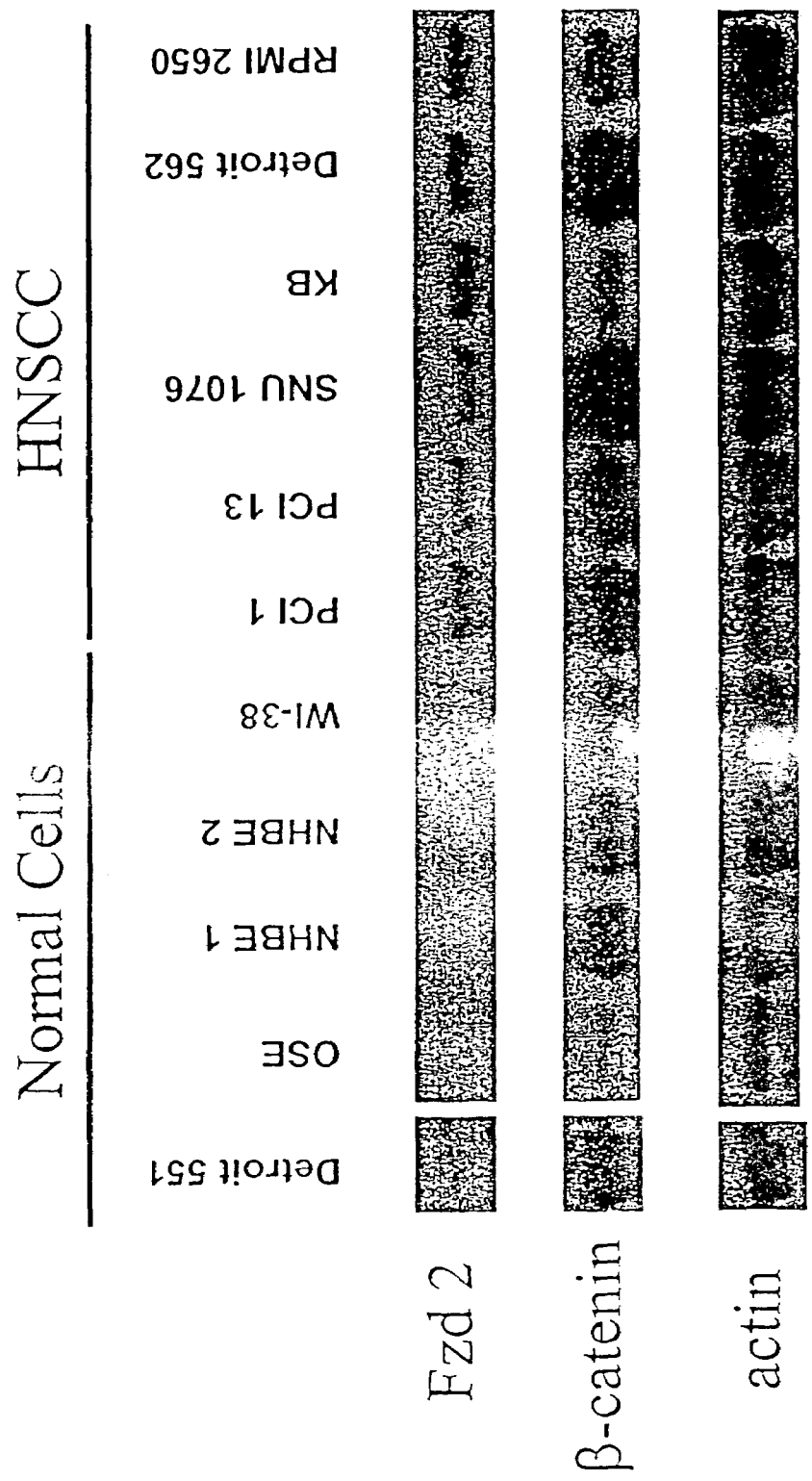

FIGS. 9A and 9B. Protein expression of FZD 2, Wnt 1, Wnt 10b, β-catenin and actin in normal and malignant cells. Normal oral squamous epithelium (OSE), normal human broncheotracheal epithelial cells (NHBE), HNSCC lines, and other solid and B cell tumor lines were lysed, separated by SDS-page, blotted onto PDVF membranes and successively probed with the indicated antibodies.

Figure 10:
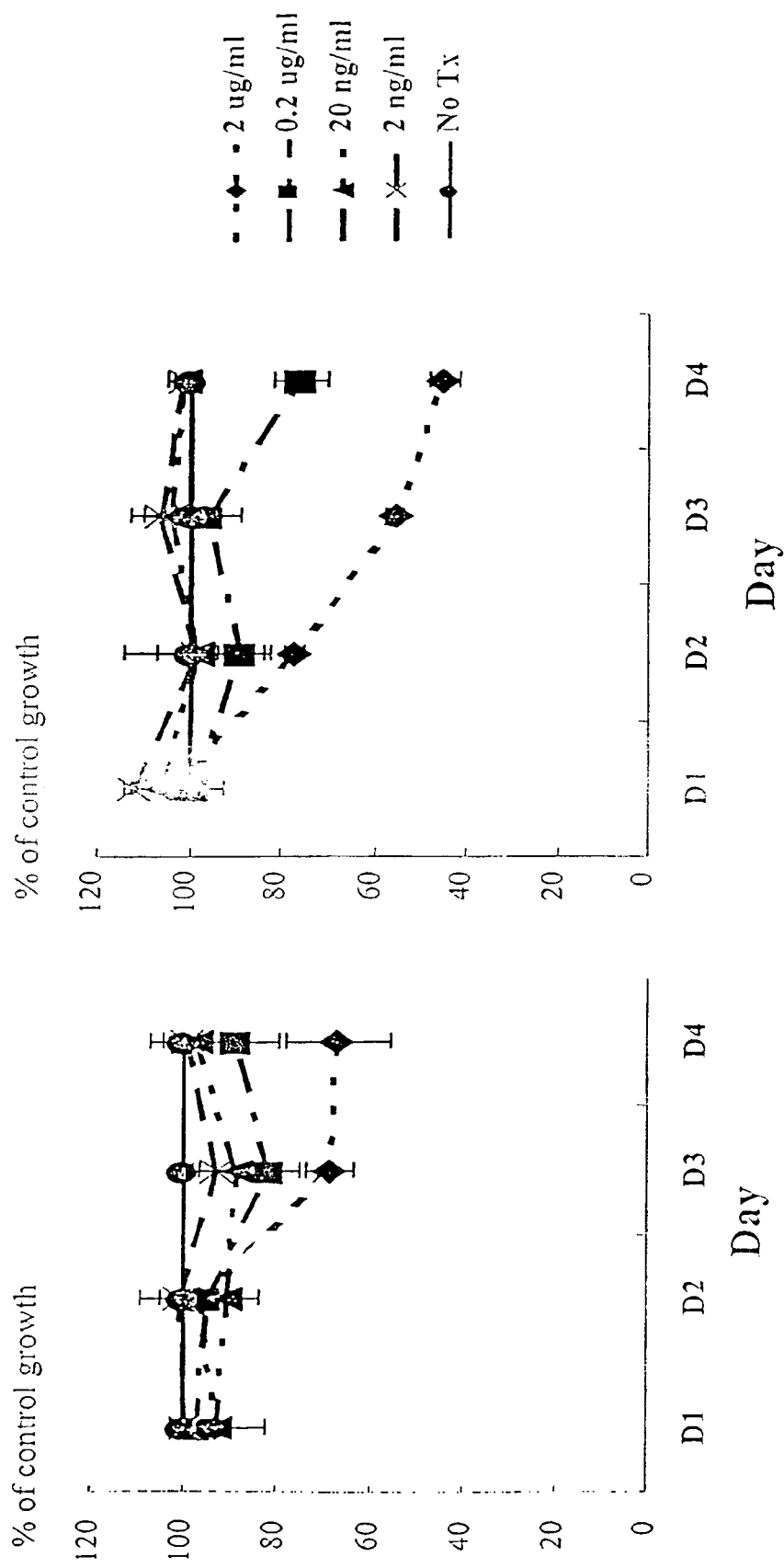
FIG. 10. Inhibition of proliferation of the SNU 1076 cell line Wnt 1 and Wnt 10b.

FIG. 10. Inhibition of proliferation of the SNU 1076 cell line. $7.5 \times 10^3$ SNU 1076 cells per well were seeded in 96 well plates. After 24 hours, graded amounts of polyclonal goat anti-human Wnt 1, Wnt 10b, or control goat anti-human IgG were added. On days 1, 2, 3, or 4, 20 µl of MTT solution was added to wells for four hours prior to lysis with 15% SDS, 0.015 M HCl. Absorbencies of 570 and 650 nm were measured. Data are expressed as the mean of at least 4 independent experiments±SD.

Figure 11:
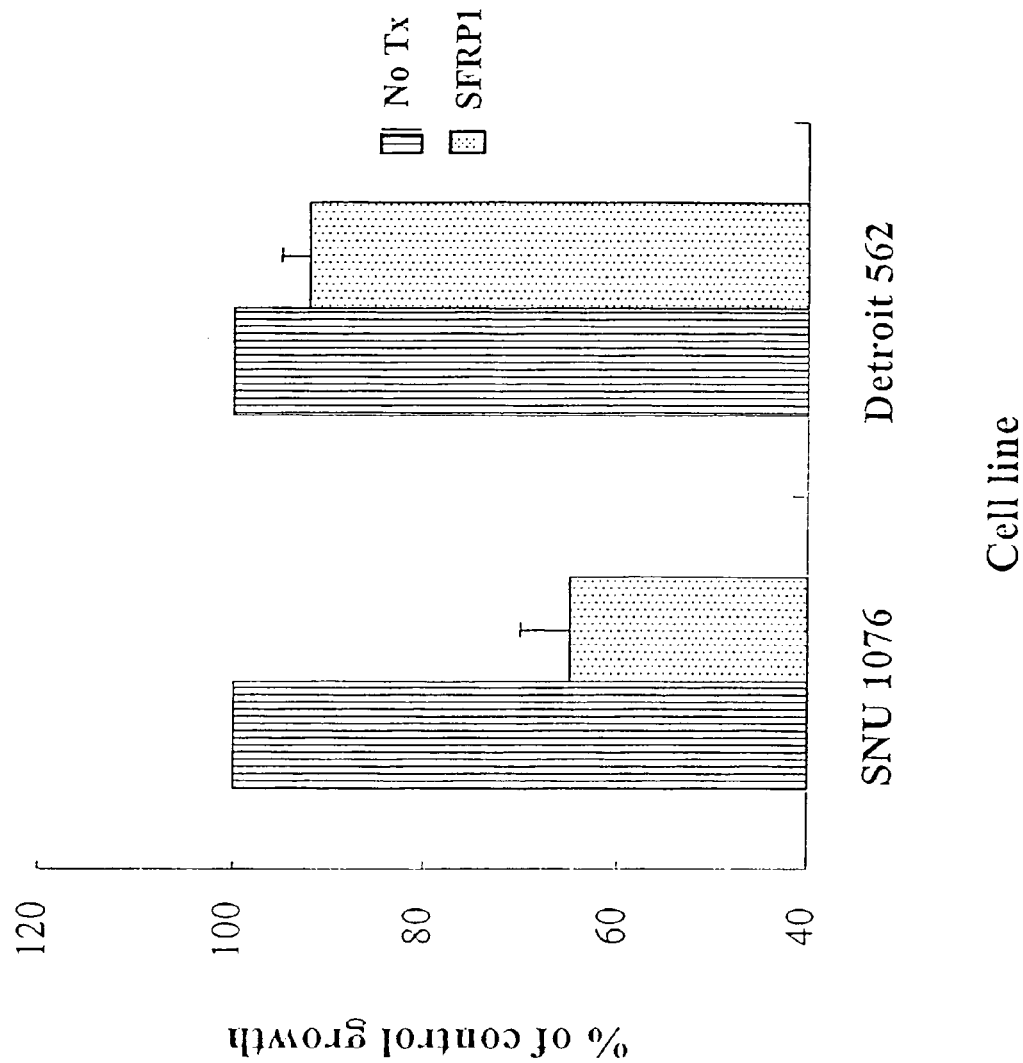
FIG. 11. Growth inhibition with a soluble WNT antagonist, secreted frizzled related protein (SFRP).

FIG. 11. Growth inhibition with a soluble WNT antagonist, secreted frizzled related protein (SFRP). Cell viability of two HNSCC lines was determined with MTT assay 72 hours after addition of 2 µg/ml of recombinant human SFRP 1. Data are expressed as the mean of 2 independent experiments±SD.

Figure 12:
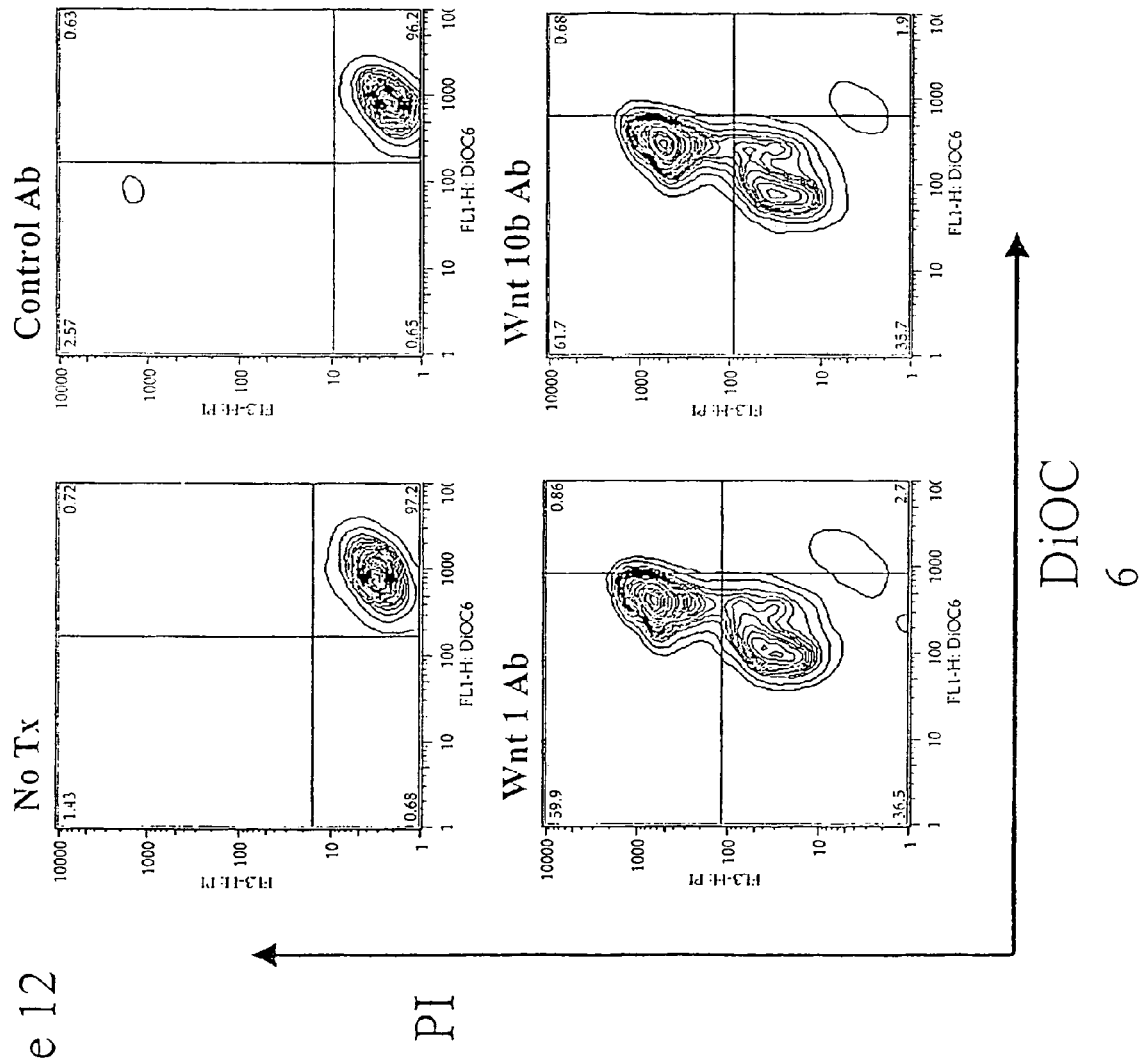
FIG. 12. Apoptotic effect of inhibition of the Wnt/Frizzled signaling pathway in a HNSCC line.

FIG. 12. Apoptotic effect of inhibition of the Wnt/Frizzled signaling pathway in a HNSCC line. SNU1076 was treated for 72 hrs with 2 µg/ml of anti-Wnt 1, Wnt 10b, or control antibodies. The cytotoxic effects of these antibodies were assessed by vital dye retention and DNA content. Cells were detached from the flasks by trypsin treatment and incubated for 10 minutes in growing medium with 5 µg/ml Propidium iodide (PI) and 40 nM $DiOC_6$ and analyzed by flow cytometry. Viable cells had high $DiOC_6$ (FL-1) and low PI (FL-3) fluorescence, and apoptotic cells had low $DiOC_6$ (FL-1) and low PI (FL-3) fluorescence.

DETAILED DESCRIPTION OF THE INVENTION

Different clonal populations of HNSCC overexpress various receptors of the Wnt and Fzd family because of their immature cell of origin and because of a growth and survival advantage provided by autocrine or paracrine Wnt/Fzd signaling. We examined HNSCC and normal human epithelial cell lines for the expression of 5 Wnt and 2 Fzd genes. The results showed that most HNSCCs did overexpress one or more Wnt and Fzd mRNAs. Moreover, the Wnt/Fzd pathway was functional in some of the HNSCC cells, as indicated by the constitutive expression of a LEF/TCF reporter gene. In the SNU 1076 cell line, anti-Wnt-1 or anti-Wnt-10b antibodies decreased the expression of β-catenin and cyclin D1, inhibited cell growth, and induced apoptosis. Thus, the Wnt and Fzd genes are frequently overexpressed in HNSCC, and are attractive targets for both immunotherapy and drug therapy.

We have examined tumor and normal cell lines for proteins that are involved in embryonic development. These studies suggest that at least one G-coupled protein receptor, frizzled 2, is overexpressed by many tumor cell lines. A broader panel of normal and malignant cells can be studied and immunization strategies can be developed directed towards passive and active immunotherapies against this antigen.

Based on the successful experience of trastuzumab as an adjunctive passive immunotherapy as described above, an evaluation of blocking the Wnt-frizzled signaling pathway on the growth of a HNSCC line with commercially available polyclonal antibodies was performed (FIGS. 4 and 5). Soluble inhibitors of frizzled have been described to induce apoptosis secondary to their inhibition of frizzled signaling (Zhou, Z. J. et al., "Up-regulation of human secreted frizzled homolog in apoptosis and its down-regulation in breast tumors," *Int J Cancer* 78:95-99 (1998)). The antibodies tested appear to have slowed the growth of the tumor line and resulted in apoptosis (FIGS. 4 and 5).

To evaluate Wnt and Fzd receptors as potential tumor associated antigens in head and neck squamous cell cancers (HNSCC), we screened various tumor and normal cell lines by both RT-PCR, and immunoblotting. Initial screening revealed that both frizzled 2 and frizzled 5 are expressed in head and neck squamous cell cancers (HNSCC), glioma, and chronic lymphocytic leukemia (CLL) (FIG. 2). Further, the results revealed that Fzd-2 was overexpressed in many HNSCC cells, compared to normal human bronchoepithelial (NHBE) cells (Table 1). The amino acid sequence of Fzd-2 is very homologous to Fzd-1 and 7 (Sagara, N. et al. "Molecular cloning, differential expression, and chromosomal localization of human frizzled-1, frizzled-2, and frizzled-7," *Biochem Biophys Res Comm* 252, 117-122 (1998)). To confirm that frizzled 2 was specifically amplified in the tumor lines to RT-PCR products from selected reactions were cloned into the TA vector (Invitrogen, Carlsbad, Calif.) and sequenced. There was 100% identity of the inserts with the human frizzled 2 sequence by BLAST search. In addition, immunoblotting showed a lack of detectable Fzd-2 protein in the lysates of NHBE in which there were weakly detectable or undetectable products by RT-PCR. The human Fzd-2 gene originally was isolated by Sagara and colleagues (Sagara 1998, infra). These investigators also found that the mRNA for Fzd-2 was not detectable in any of 15 different normal human adult tissues, with the possible exception of heart. In contrast, embryonic tissues, as well as six of eight malignant cell lines, expressed abundant Fzd-2 mRNA. However, these investigators did not test for the expression of frizzled Fzd-2 protein, and mRNA levels do not necessarily correlate with protein expression. Our studies show that Fzd-2 protein expression is prominent in HNSCC cell lines, when compared to normal NHBE cells. Hence, antibodies against specific determinants of the extracellular domain of Fzd-2 could be used to bind to and target such malignant cells.

Compared to NHBE cells, the HNSCC cell lines expressed much higher message levels of Wnt-1, Wnt-5a, Wnt-10b and Wnt-13. Of these Wnt proteins Wnt-1, 5A, and 10b were exclusively expressed by the malignant cell lines and were not detected in the normal tissues tested. Immunoblotting experiments confirmed the overexpression of Wnt-1 and Wnt-10b protein in several HNSCC cell lines (FIG. 3). Since the tumors had high levels of both the ligands and their Fzd-2 receptors, it was important to determine if Wnt/Fzd signaling was constitutively active in the HNSCC cells. The canonical Wnt/Fzd signaling cascade leads to the accumulation of cytoplasmic β-catenin and its translocation to the nucleus. In the nucleus beta-catenin binds a specific sequence motif at the N terminus of lymphoid-enhancing factor /T cell factor (LEF/TCF) to generate a transcriptionally active complex (Behrens J et al. "Functional interaction of beta-catenin with the transcription factor LEF-1," *Nature* 382, 638-642 (1996)). Experiments using LEF/TCF reporter gene, TOPFLASH, demonstrated that LEF/TCF dependent transcription was active in the SNU 1076 cells.

The Wnt/frizzled pathway has been previously implicated in tumorigenesis. Soluble Wnt glycoproteins have been demonstrated to transmit signal by binding to the seven transmembrane domain G-protein coupled-receptor frizzled (FIG. 1) (Bhanot, P. et al. "A new member of the frizzled family from Drosophila functions as a Wingless receptor," *Nature* 382:225-230 (1996); Yang-Snyder, J. et al. "A frizzled homolog functions in a vertebrate Wnt signaling pathway," *Curr Biol* 6:1302-1306 (1996); Leethanakul, C. et al. "Distinct pattern of expression of differentiation and growth-related genes in squamous cell carcinomas of the head and neck revealed by the use of laser capture microdissection and cDNA arrays," *Oncogene* 19:3220-3224 (2000)). Upon Wnt signaling, a cascade is initiated that results in the accumulation of cytoplasmic beta-catenin and its translocation to the nucleus. In the nucleus beta-catenin binds a specific sequence motif at the N terminus of lymphoid-enhancing factor /T cell factor (LEF/TCF) to generate a transcriptionally active complex (Behrens, J. et al. "Functional interaction of beta-catenin with the transcription factor LEF-1," *Nature* 382:638-642 (1996)). Beta-catenin interacts with multiple other proteins such as cadherin, which it links to the cytoskeleton (Hoschuetzky, H. et al. "Beta-catenin mediates the interaction of the cadherin-catenin complex with epidermal growth factor receptor," *J Cell Biol* 127:1375-1380 (1994); Aberle, H. et al., "Assembly of the cadherin-catenin complex in vitro with recombinant proteins," *J Cell Sci* 107:3655-3663 (1994)). It also associates with the adenomatous polyposis coli (APC) tumor suppressor protein and glycogen synthetase 3 beta (GSK3β) (Rubinfeld, B. et al., "Binding of GSK3beta to the APC-beta-catenin complex and regulation of complex assembly," *Science* 272:1023-1026 (1996)). These proteins function to negatively regulate beta catenin by facilitating phosphorylation near the aminoterminus and thus accelerating its proteolytic degradation (Yost, C. et al., "The axis-inducing activity, stability, and subcellular distribution of beta-catenin is regulated in Xenopus embryos by glycogen synthase kinase 3," *Genes Dev* 10:1443-1454 (1996)).

A panel of tumor cells that can be screened are derived from the panel of 60 lines which are being characterized in the national Institutes of Health Developmental Therapeutics program. The cell lines that are currently available include: (Non-small Cell Lung Cancer) A549/ATCC, NCI-H226, NCI-H460, HOP-62, HOP-92, (colon cancer) HT29, HCT-116, (breast cancer) MCF7, NCI/ADR-RES, MDA-MB-231/ATCC, T-47D, (ovarian cancer) OVCAR-3, OVCAR-4, SK-OV-3, (leukemia) CCRF-CEM, K-562, MOLT-4, HL-60 (TB), RPMI-8226, (renal cell) 786-0, TK-10, (prostate cancer) PC-3, DU-145. Normal control cell lines can be purchased from Clonetics.

Although Wnt and Fzd were expressed in HNSCC cells, they may be dispensable for cell growth and survival. Therefore, the effects of antibodies to the extracellular domains of Wnt-1 and Wnt-10b were studied in three HNSCC lines known to express the receptors. When compared to control antibodies, both anti-Wnt antibodies slowed the growth of one of the HNSCC cell lines (SNU 1076) and resulted in apoptosis. Treatment with high levels of SFRP1, a Wnt antagonist, exerted a similar effect. Moreover, interference with Wnt/frizzled signaling in SNU 1076 cells decreased the activity of the LEF/TCF reporter gene, and reduced levels of (β-catenincyclin D1 and fibronectin. These results suggest that continued autocrine or paracrine Wnt/Fzd signaling may be required for the growth and survival of a subset of HNSCC cells.

These results suggest that antibodies against Wnt and frizzled receptors may exert two different effects in HNSCC cancers in vivo. In malignant cells that depend on Wnt/Fzd signaling for survival, the antibodies might directly slow tumor growth and/or induce apoptosis. In HNSCC cells that incidentally overexpress the receptors, but do not require them for proliferation, the antibodies still could potentially target the tumor cells for killing by complement, or antibody dependent cellular toxicity. Based on these data, we believe that passive immunotherapy could be a useful adjunctive therapy in HNSCC that overexpress one or more Wnt and Fzd receptors.

Experimental Methods

Cell lines and culture: Ten HNSCC, 2 B lymphoma, and 2 glioblastoma cell lines were studied. Detroit-562 (pharyngeal cancer), KB (carcinoma in the floor of the mouth), RPMI-2650 (nasal septal) cancer), SCC-25 (tongue cancer), U87MG and U373MG (glioblastoma), Ramos (lymphoma), Detroit-551 (human skin fibroblast-like cells) and WI-38 (human lung fibroblasts) were purchased from the American Type Culture Collection (Manassas, Va.). The PCI-1, 13, and 50 cell lines were kindly provided by Dr. T. Whiteside (Univ. of Pittsburgh, Pa.) (Whiteside, T. L. et al., "Human tumor antigen-specific T lymphocytes and interleukin-2-activated natural killer cells: comparisons of antitumor effects in vitro and in vivo," *Clin Cancer Res.* 4, 1135-1145 (1998); Yasumura, S. et al., "Human cytotoxic T-cell lines with restricted specificity for squamous cell carcinoma of the head and neck," *Cancer Res.* 53, 1461-1468 (1993)). The HNSCC cell lines SNU 1066, SNU 1076 and AMC 4 cell lines were provided by Dr. J. G. Park (Seoul National University, Korea) and Dr. S. Y. Kim (University of Ulsan, Korea), respectively (Ku, J. L. et al., "Establishment and characterization of human laryngeal squamous cell carcinoma cell lines," *Laryngoscope* 109, 976-82 (1999); Kim, S. Y. et al. "Establishment and characterization of nine new head and neck cancer cell lines," *Acta Otolaryngol.* 117, 775-784 (1997)). Two different normal human tracheobronchial epithelial (NHBE) cells derived from different persons were purchased from Clonetics (San Diego, Calif.). All cancer cell lines were cultured at 37° C. in a humidified atmosphere of 5% $CO_2$, in either RPMI 1640, DMEM (Dulbecco's modified Eagle's medium), or Ham's 12-DMEM medium, as recommended by the suppliers, supplemented with 10% fetal bovine serum. NHBE cells were cultured in the bronchial epithelial cell growth media provided by the company. Normal epithelial cells were obtained from scrapings of the oral mucosa of 10 normal healthy volunteers. All cell lines were found to be free of mycoplasma contamination.

RT-PCR Analyses: Total RNA was extracted by using Trizol® (Gibco BRL, Grand Island, N.Y.), according to the manufacturer's directions. Different pairs of gene-specific primers based on GenBank sequences of cloned human Wnt and Fzd genes were used for reverse transcriptase-PCR(RT-PCR) analysis. Reverse transcription was performed with a Superscript™ Preamplification kit (Gibco BRL). One microgram of RNA was used from each sample, and 25-35 cycles of PCR were carried out. The PCR products were separated by electrophoresis, visualized under ultra violet light, and scanned with a laser densitometer. The intensities of the Wnt and Fzd bands were compared with the amplicon of the housekeeping gene G3PDH. Preliminary experiments confirmed that the PCR amplifications had not reached a plateau for all data reported in the results. The following list summarizes the primer pairs used:

Fzd-2: 5'-cagcgtettgcccgaccagatcca-3'(reverse); 5'-ctagcgccgctettcgtgtacctg-3' (forward). Fzd-5: 5'-ttcatgtgc-ctggtggtgggc-3' (forward); 5'-tacacgtgcgacagggacacc-3' (reverse). Wnt-1: 5'-cacgacctcgtctacttcgac-3' (forward); 5'-acagacactcgtgcagtacgc-3' (reverse). Wnt-5a: 5'-acacctctttccaaacaggcc-3' (forward); 5'-ggattgttaaactcaactctc-3' (reverse) Wnt-7a: 5'-cgcaacaagcggcccaccttc-3' (forward), 5'-tccgtgcgctcgctgcacgtg-3' (reverse) Wnt-10b: 5'-gaatgcgaatccacaacaacag-3' (forward); 5'-ttgcggttgtgggtat-caatgaa-3'(reverse). Wnt-13: 5'-aagatggtgccaacttcaccg-3' (forward); 5'-ctgccttcttggggggetttgc-3'(reverse) G3PDH: 5'-accacagtccatgccatcac-3' (forward); 5'-tacagcaacagggtg-gtgga-3'(reverse).

The specificities of the Wnt and Fzd PCR products were confirmed by cloning and sequencing the products, using a TOPO TA Cloning kit and M13 primers (Invitrogen, Carlsbad, Calif.).

Immunoblotting: After removal of medium, cells in logarithmic growth were disrupted in lysis buffer [25 mM Tris HCl, 150 mM KCl, 5 mM EDTA, 1% NP-40, 0.5% sodium deoxycholic acid, 0.1% sodium dodecyl sulfate] including phosphatase and protease inhibitor cocktails. Each lane of an SDS-PAGE gel was loaded with 20 μg of protein. After electrophoresis, the proteins were transferred to a polyvinylidene difluoride (PVDF) membrane, blocked with 2% I-block™ (Tropix Inc, Bedford, Mass.) containing 0.05% Tween-X in PBS, and then incubated with primary antibody. Horseradish peroxidase-conjugated anti-IgG (Santa Cruz Laboratories, Santa Cruz, Calif.) was used as the secondary antibody. The membranes were developed using a chemiluminescence system (ECL detection reagent: Amersham Life Science, Aylesbury, UK), and scanned with a laser densitometer. The membranes were stripped with Re-Blot™ Western blot recycling kit (Chemi-Con International Inc, Temecula, Calif.) and reprobed using other antibodies and actin monoclonal antibody (Chemi-Con International Inc) as a control. Prestained molecular weight markers (New England Biolabs, Beverly, Mass.) were used as reference.

Antibodies: Polyclonal antibodies specific for the amino terminal extracellular domains of Wnt-1 and Wnt-10b, and for the carboxy terminal region of Fzd-2, were purchased from Santa Cruz Laboratories, and monoclonal antibodies specific for β-catenin and fibronectin were purchased from Transduction Laboratories (Lexington, Ky.). Antibodies to cyclin D1 and actin were purchased from PharMingen (San Diego, Calif.) and Chemi-Con International Inc., respectively. Purified recombinant human soluble frizzled-related protein-1 was prepared in Dr. J. Rubin's laboratory as described previously (Uren, A. et al., "Secreted frizzled-related protein-1 binds directly to Wingless and is a biphasic modulator of Wnt signaling," *J Biol. Chem.* 275, 4374-4382 (2000)).

MTT (3-[4,5-dimethylthiazol-2-yl]-2,5-diphenyl tetrazolium bromide)-based cell assay: Cell proliferation was determined by a colorimetric MTT assay. Briefly, either 7.5–10× $10^3$ cells were dispersed in each well of a 96 well plate. Twenty-hours after culture, 4 different concentrations of anti-Wnt-1 or ant-Wnt-10b antibody (2 μg/ml, 0.2 μg/ml, 20 ng/ml, and 2 ng/ml) were added to the cultures. The same concentrations of goat antihuman IgG (Fisher Scientific) were used as an isotype control. The antibodies were dialyzed against tissue culture medium prior to use, to remove preservatives. On 1, 2, 3, or 4 days after incubation, 20 μl of MTT solution was added to each well. Four hours later the cells were lysed, and absorbances at 570 nM and 650 nM were measured and growth, as a percentage of control, was determined from the formula:

$$\% \text{ of control growth} = (B-A)/(C-A) \times 100$$

where A=absorbance at start of incubation, B=absorbance after incubation with antibodies tested, C=absorbance after incubation with control antibody. The assays were performed in triplicate, and the results represent the mean value±standard deviation from four independent experiments.

Flow Cytometry: Cell apoptosis was assayed by propidium iodide (PI) and $DiOC_6$ staining, followed by flow cytometry. The HNSCC line, SNU1076, was treated with 2 µg/ml anti-Wnt-1, anti-Wnt-10, or control IgG for 72 hrs. Cells were detached from the flasks by trypsin treatment and incubated for 10 minutes in medium with 5 µg/ml PI and 40 nM $DiOC_6$, and then were analyzed by flow cytometry in a FACS caliber (Becton-Dickinson, San Jose, Calif.). Viable cells had high $DiOC_6$ (FL-1) and low PI (FL-3) fluorescence, whereas apoptotic cells had low $DiOC_6$ (FL-1) and low PI (FL-3) fluorescence.

Tumor and normal cell lines can be identified that express frizzled 2. Ten cell lines that express frizzled 2 and at least two cell lines that do not are currently being tested. The cells will be plated as described above for FIG. 4. The mouse sera that tests for highest titer and specificity in aim 2 will be used in the cell cultures. The cells will be exposed to graded amounts of polyclonal anti-frizzled 2 mouse sera and normal control serum. On days 1, 2, 3, and 4 subsets of the replicate wells will be assayed for proliferative capacity. On successive days 20 µl of MTT (3-[4,5-dimethylthiazol-2-yl]-2,5-diphenyl tetrazolium bromide)-based solution will be added to wells for four hours prior to lysis with 15% SDS, 0.015 M HCl. Absorbencies of 570 and 650 nm will measured. These measurements will be performed in triplicate and statistical relevance will be assessed by Students t test for $P<0.05$.

The selected cell lines will also undergo analysis for DNA content by Propidium iodide (PI) staining. Cell lines treated for 72 hours in the presence of graded concentrations of normal or immunized mouse serum will be trypsinized, incubated for 10 minutes with 5 µg/ml PI and 40 nM $DiOC_6$, and analyzed by flow cytometry. Viable cells will be $DiOC_6$ (FL-1) high and PI (FL-3) low, and apoptotic cells will be $DiOC_6$ (FL-1) low and PI (FL-3) low. Additionally, cells will detached from the flasks with trypsin and incubated overnight in a hypotonic buffer (0.1% citrate, 0.1% SDS) containing 50 µg/ml PI and 100 µg/ml RNase. The amount of DNA will be measured by flow cytometry. Apoptotic cells are defined as having a DNA content lower than the $G_0G_1$ levels (sub-$G_0$ cells).

Transient Luciferase Assays: The pTOPFLASH-Luc reporter gene vector and the pFOPFLASH-Luc control were kindly provided by Dr. Hans Clevers (University Medical Center Utrecht, The Netherlands). For TOPFLASH/FOPFLASH reporter gene assays, SNU 1076 cells were cotransfected with 0.5 µg of pTOPFLASH-Luc or pFOPFLASH-Luc and 0.5 µg of pCMV-βGal, as described previously (Korinek, V. et al., "Constitutive transcriptional activation by a beta-catenin-Tcf complex in APC –/– colon carcinoma," *Science* 275, 1784-1787 (1997)). Cells were harvested 24 h after transfection, disrupted in lysis buffer, and luciferase and β-galactosidase activities were determined using the Dual-Light reporter gene assay system (Applied Biosystems, Foster City, Calif.). Luciferase activities of each pTOPFLASH-Luc or pFOPFLASH-Luc transfected culture, and the β-galactosidase activities of pCMV-βGal transfected cells, were measured in the same samples using a luminometer. The transfection efficiencies of the samples were normalized by the activity of β-galactosidase.

Other features and advantages of the invention will be apparent from the detailed description and from the claims.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

Immunogenicity of Isolated Non-Homologous Regions of Frizzled 2

The first extracellular domain of frizzled 2 contains a region which based on protein structure is least homologous to the other frizzled protein family members (FIG. 6) (Sagara, N. et al. "Molecular cloning, differential expression, and chromosomal localization of human frizzled-1, frizzled-2, and frizzled-7," *Biochem Biophys Res Commun* 252:117-122 (1998)). This polypeptide sequence may have sufficient ternary structure to generate an antibody response to the native protein. In order to enhance B cell stimulation this epitope will be coupled to T cell epitopes that have been described to generate T cell help.

The overall strategy will be to use the least conserved region of the frizzled protein, attempting to preserve the most native structure possible and to generate the most potent immune response. The most versatile method for designing vaccines of defined regions is naked plasmid DNA. The advantages are that the vectors can be rapidly redesigned to change the length of sequence that is expressed, discontinuous regions of the protein can be co-expressed, and the DNA sequence of the protein can be fused to other epitopes to enhance antigenicity (O'Hern, P. A. et al. "Colinear synthesis of an antigen-specific B-cell epitope with a 'promiscuous' tetanus toxin T-cell epitope: a synthetic peptide immunocontraceptive," *Vaccine* 15:1761-1766 (1997); Paterson, M. et al., "Design and evaluation of a ZP3 peptide vaccine in a homologous primate model," *Mol Hum Reprod* 5:342-352 (1999); Dakappagari, N. K. et al., "Prevention of mammary tumors with a chimeric HER-2 B-cell epitope peptide vaccine," *Cancer Res* 60:3782-3789 (2000)). It affords the versatility of expressing soluble, membrane bound proteins, or small peptide fragments. Also gene transfer by this technique is a powerful tool to introduce multiple protein elements into the same or separate locations. In this system single or multiple proteins can be locally expressed. Injecting a combination of plasmids expressing antigens and costimulators like B7.1 and B7.2 results in enhanced immune responses (Corr, M. et al., "Costimulation provided by DNA immunization enhances antitumor immunity," *J Immunol* 159:4999-5004 (1997); Chan, K. et al., "The roles of mhc class ii, cd40, and b7 costimulation in ctl induction by plasmid dna (DNA?)," *J Immunol* 166:3061-3066 (2001)).

Several plasmids have been constructed which are under the control of the cytomegalovirus (CMV) promoter which has been found to enable high levels of antigen expression in injected muscle. The pCMVint vector includes the cytomegalovirus (CMV) E1 promoter, the simian virus (SV40) t-intron, and the SV-40 polyadenylation site (Corr, M. et al. "Gene vaccination with naked plasmid DNA: mechanism of CTL priming," *J Exp Med* 184:1555-1560 (1996)). The ACB vector has the same elements except the polyadenylation sequence is from the bovine growth hormone gene (Sato, Y. et al. "Immunostimulatory DNA sequences necessary for effective intradermal gene immunization," *Science* 273:352-354 (1996)). The first set of plasmid constructs planned will encode the least homologous region of the frizzled 2 between the ninth and tenth cysteines. These cysteines will be preserved in this series of constructs as they may stabilize a configuration that enables antibody binding to the native protein. This polypeptide fragment will be fused at the aminoterminus or the carboxylterminus via a short linker to a tetanus toxin or measles virus fusion (MVF) protein T helper epitopes (see below) (O'Hern, P. A. et al. "Colinear synthesis of an antigen-specific B-cell epitope with a 'promiscuous' tetanus toxin T-cell epitope: a synthetic peptide immunocontraceptive," *Vaccine* 15:1761-1766 (1997); Paterson, M. et al. "Design and evaluation of a ZP3 peptide vaccine in a homologous primate model," *Mol Hum Reprod* 5:342-352 (1999); Dakappagari, N. K. et al., "Prevention of mammary tumors with a chimeric HER-2 B-cell epitope peptide vaccine," *Cancer Res* 60:3782-3789 (2000)). These minigenes will be constructed with overlapping oligonucleotides. The oligonucleotides are 5' prime phosphorylated with T4 kinase at room temperature for 30 minutes, annealed by boiling an equimolar admixture of two complementary oligomers and slow cooling. The double stranded oligonucleotides are then ligated 3' to the tissue plasminogen leader (TPA) leader into the EcoR47III site in frame and into the BamHI site of the pBluescript SKII vector. The minigene is then subcloned into the pCMV and pACB vectors between the Pst1 and Xba1 sites as previously described (Corr, M. et al., "Costimulation provided by DNA immunization enhances antitumor immunity," *J Immunol* 159:4999-5004 (1997)).

The inserts for the vectors are designed as described above. The frizzled putative B cell epitope is from the published sequence. The tetanus toxin and measles MVF T helper epitopes have been optimized for human codon usage by the most frequently used codon per amino acid. The DNA constructs have an initiating methionine and stop codons added to the 5' and 3' ends respectively. The aminoacid and DNA sequences are summarized below with the short GPSL linker sequence in bold and the T cell helper epitope underlined.

Tetanus toxin epitope fused to a frizzled domain pFZD2-TT

MCVGQNHSEDGAPALLTTAPPPGLQPGAGGTPGGPGGGAPPRYATLEHPFHC

-GPSL-VDDALINSTKIYSYFPSV-STOP

ATG TGC GTC GGC CAG AAC CAC TCC GAG GAC GGA GCT CCC GCG CTA CTC ACC ACC

GCG CCG CCG CCG GGA CTG CAG CCG GGT GCC GGG GGC ACC CCG GGT GGC CCG GGC

GGC GGC GGC GCT CCC CCG CGC TAC GCC ACG CTG GAG CAC CCC TTC CAC TGC-GGC

CCC AGC CTG- GTG GAC GAC GCC CTG ATC AAC AGC ACC AAG ATC TAC AGC TAC TTT

CCC AGC GTG TAG pTT-FZD2

MVDDALINSTKIYSYFPSV-GPSL-

CVGQNHSEDGAPALLTTAPPPGLQPGAGGTPGGPGGGAPPRYATLEHPFHC-STOP

ATG GTG GAC GAC GCC CTG ATC AAC AGC ACC AAG ATC TAC AGC TAC TTT CCC AGC

GTG-GGC CCC AGC CTG-TGC GTC GGC CAG AAC CAC TCC GAG GAC GGA GCT CCC GCG

CTA CTC ACC ACC GCG CCG CCG CCG GGA CTG CAG CCG GGT GCC GGG GGC ACC CCG

GGT GGC CCG GGC GGC GGC GGC GCT CCC CCG CGC TAC GCC ACG CTG GAG CAC CCC

TTC CAC TGC TAG

Measles MVF epitope fused to a frizzled domain

PFZD2-MMVF

MCVGQNHSEDGAPALLTTAPPPGLQPGAGGTPGGPGGGAPPRYATLEHPFHC-GPSL-

KLLSLIKGVIVHRLEGVE-STOP

ATG TGC GTC GGC CAG AAC CAC TCC GAG GAC GGA GCT CCC GCG CTA CTC ACC ACC

GCG CCG CCG CCG GGA CTG CAG CCG GGT GCC GGG GGC ACC CCG GGT GGC CCG GGC

GGC GGC GGC GCT CCC CCG CGC TAC GCC ACG CTG GAG CAC CCC TTC CAC TGC-GGC

CCC AGC CTG- AAG CTG CTG AGC CTG ATC AAG GGC GTG ATC GTG CAC CGC CTG GAG

GGC GTG GAG TAG

PMMVF-FZD2

-continued

```
MKLLSLIKGVIVHRLEGVE-GPSL-

CVGQNHSEDGAPALLTTAPPPGLQPGAGGTPGGPGGGGAPRYATLEHPFHC-STOP

ATG AAG CTG CTG AGC CTG ATC AAG GGC GTG ATC GTG CAC CGC CTG GAG GGC GTG

GAG-GGC CCC AGC CTG-TGC GTC GGC CAG AAC CAC TCC GAG GAC GGA GCT CCC GCG

CTA CTC ACC ACC GCG CCG CCG CCG GGA CTG CAG CCG GGT GCC GGG GGC ACC CCG

GGT GGC CCG GGC GGC GGC GGC GCT CCC CCG CGC TAC GCC ACG CTG GAG CAC CCC

TTC CAC TGC TAG
```

Plasmid DNA is prepared using Qiagen Maxiprep (Chatsworth, Calif.) kits with the modification of adding one tenth volume 10% Triton X-114 (Sigma, St. Louis, Mo.) to the clarified bacterial lysate prior to applying it to a column. Prior to injection the residual endotoxin level is quantified using a limulus extract clot assay (Associates of Cape Cod, Woods Hole, Mass.). A level of ≦5 ng endotoxin/vg DNA need be obtained prior to use in an animal (Corr, M. et al. "In vivo priming by DNA injection occurs predominantly by antigen transfer," *J Immunol* 163:4721-4727 (1999)). The DNA is resuspended in a sterile pyrogen free saline solution for injection.

Twenty-eight female mice will be divided into groups of 4 mice each. They will be injected in the dermis of the tail with a combination of 50 μg plasmid encoding a costimulator (B7-1 or B7-2) and 50 μg linker plasmid diluted in normal saline at weeks zero, one and two. A group with empty vector is included as a negative control. The groups are as follows:

| Group | Plasmid 1 | Plasmid 2 |
|-------|-----------|-----------|
| A | pTT-FZD2 | nCMV |
| B | pTT-FZD2 | nCMVB7-1 |
| C | pTT-FZD2 | nCMVB7-2 |
| D | pFZD2-TT | nCMV |
| E | pFZD2-TT | nCMVB7-1 |
| F | pFZD2-TT | nCMVB7-2 |
| G | — | nCMV |

Another group of mice in similar groups will be immunized using the pMMVF-FZD2 and pFZD2-MMVF set of linked epitope plasmids. The nCMVB7-1 and nCMVB7-2 constructs encode the cDNAs for murine CD80 and CD86, which were kindly provided by G. Freeman (Dana-Farber Cancer Institute, Boston, Mass.) (Corr, M. et al., "Costimulation provided by DNA immunization enhances antitumor immunity," *J Immunol* 159:4999-5004 (1997)).

Mice will be bled prior to the start of the experiment and then every two weeks thereafter. Serum will be separated and stored at −20° C. prior to testing. On week ten (seven weeks after the last injection) mice will be sacrificed. The titers of antibody will be tested by anti-peptide ELISA. Ninety-six well plates (Costar) are coated with 50 μl/well 20 μg/ml peptide in phosphate buffered saline (PBS) overnight at 4° C. The plates are then washed and blocked with 200 μl/well 2% bovine serum albumin (BSA) in PBS. Sera are diluted in 2% BSA in PBS. After overnight incubation at 4° C. the plates are washed. Bound murine IgG is detected by alkaline phosphatase conjugated-goat anti-murine IgG (Jackson Immunoresearch Laboratories) followed by p-nitrophenylphosphate substrate. The titration curves for each sera are compared using DeItaSOFT II v. 3.66 (Biometallics, Princeton, N.J.).

Mice that develop sufficiently high titers of antibody that bind to the peptide will be tested for specificity to frizzled 2 by fluorescent cytometry with cells that express the protein by transfection and known tumor cells that have the mRNA. We will also test the binding by Western blot analysis of cells that express this isoform and to cells that have been found to express other frizzled family members. Briefly, immunoblotting will be performed as described above. Cells are lysed in with a solution containing 25 mM Tris HCl, 150 mM KCl, 5 mM EDTA, 1% NP-40, 0.5% sodium deoxycholic acid, 0.1% sodium dodecyl sulfate, 1 mM NaVO$_3$, 1 mM NaF, 20 mM β-glycerophosphate and protease inhibitors. Twenty μg of protein from each cell line is separated by SDS-PAGE and transferred to a PVDF membrane. The membrane is soaked in 2% I-block, 0.05% Tween X in PBS and then incubated with a 1:500 dilution of polyclonal pre or post immunization mouse serum at 1:500 dilution. Murine antibody binding is then detected by horseradish peroxidase-conjugated rat anti-mouse IgG and chemiluminescence (ECL detection reagents). To verify relative amount of protein transferred in each lane, the blots are then stripped and the presence of actin is measured with an actin monoclonal antibody.

Different immunization strategies are being evaluated for their efficacy in eliciting a humoral immune response. If the antibody response is weak then the vectors can be redesigned with other known potent T helper epitopes. Other vectors can be designed where the polypeptide from frizzled 2 is shorter and does not contain the cysteines, which may be inhibiting the most desirable conformation. Another immunization strategy will be to use a prime boost method. The animals are originally injected with plasmid DNA and then are boosted with peptide or recombinant protein in incomplete Freund's adjuvant. The B-cell epitope in each construct may need to be redesigned until there is no cross-reactivity in the humoral response to other frizzled isoforms.

Example 2

Expression of Wnt and Fzd mRNAs in HNSCC

Ten different HNSCC cell lines, two normal human broncho-epithelial (NHBE) cell lines, and normal oral squamous epithelial cells were tested by RT-PCR for the expression of five Wnts (Wnt-1, Wnt-5a, Wnt-7a, Wnt-10b, Wnt-13), and two Fzds (Fzd-2 and 5). Representative results are illustrated in FIG. 8 and are summarized in Table 1. When compared to the housekeeping gene G3PDH, all the Wnts, as well as Fzd-2, were expressed more frequently in HNSCC than in normal cells, while there was no difference in Fzd-5 gene expression. Of the Wnt genes, Wnt-1,5a, and 10b were most strongly expressed by the malignant cells, but were barely detectable in the normal tissues tested. We then investigated further Wnt-1 and Wnt-10b, since these Wnts signal through the canonical β-catenin and LEF/TCF, and because antibodies to the extracellular domains were available.

Example 3

Expression of Wnt/Fzd proteins in HNSCC

Cell lines were lysed and analyzed for Wnt-1, Wnt-10b, Fzd-2, and β-catenin protein expression by immunoblotting (FIG. 9). The normal cells expressed much less of these Wnt or Fzd proteins, when compared to the tested HNSCC, with the exception of RPMI 2650. Of note is the lack of detectable Fzd protein in the lysate of the NHBE cell line that had a weakly detectable product by RT-PCR. Beta-catenin was detected in all the samples, including both HNSCC and NHBE lines.

Example 4

Effects of Anti-Wnt Antibodies and SFRPI

Treatment with antibody against the extracellular domains of Wnt-1 or Wnt-10b decreased the proliferation of the SNU1076 HNSCC cell line (FIG. 10), while little effect was observed in PCI 13 cells (data not shown). The inhibition of cell growth by the antibodies was dependent on the concentration and incubation time. The treatment of the SNU1076 HNSCC cell line with anti-Wnt antibodies, but not control antibody, also induced apoptosis (FIG. 12). Similar to anti-Wnt antibodies, treatment with recombinant SFRP1 protein (2 μg/ml), a natural antagonist of Wnt signaling, inhibited growth of SNU 1076 cells (FIG. 11).

To determine if the effects of anti-Wnt antibody on SNU1076 cells were related to inhibition of Wnt signaling, we compared levels of the Wnt regulated genes cyclin D1 and fibronectin (FIG. 7A). The anti-Wnt-1 antibody, but not the control IgG, reduced cyclin D1, fibronectin, and β-catenin levels in the cytosol of SNU 1076 cells. To confirm these results, TOPFLASH-Luc, a reporter plasmid containing TCF/LEF binding sites, or FOPFLASH-Luc, a negative control plasmid having mutant binding sites was introduced into SNU 1076 cells together with the pCMV-β-gal plasmid (to assess transfection efficiency). Luciferase activity was higher in the TOPFLASH than the FOPFLASH transfected cells, indicating that LEF/TCF dependent transcription was constitutively active. Cells transfected with FOPFLASH showed no changes in the low baseline luciferase activity after treatment with anti-Wnt1 antibodies, whereas cells transfected with TOPFLASH displayed decreased luciferase activity (FIG. 7B).

Example 5

Effects of Anti-Frizzled Antibodies

Wnt signaling through frizzled receptors has been described to inhibit apoptosis (Chen, S. et al. "Wnt-1 signaling inhibits apoptosis by activating beta-catenin/T cell factor-mediated transcription," *J Cell Biol* 152:87-96 (2001)). Also some of the genes that are regulated by TCF/beta-catenin are known to be associated with the cell cycle and cellular proliferation. By blocking the binding of Wnt proteins to their receptors via antibodies directed to the extracellular portion of frizzled this pathway can be interrupted. Decreasing the downstream translocation of beta-catenin to the nucleus could result in slower tumor growth or death of the cell.

The immunization strategy that may be useful in terms of raising specific antibodies that delay growth in cell culture will then be tested for potential in vivo efficacy in mice. Previously we have used the H-$2^b$ thymoma line EL4 as a syngeneic tumor in C57B 1/6 mice (Corr, M. et al., "Costimulation provided by DNA immunization enhances antitumor immunity," *J Immunol* 159:4999-5004 (1997); (Cho, H. J. et al., "Immunostimulatory DNA-based vaccines induce cytotoxic lymphocyte activity by a T-helper cell-independent mechanism," *Nat Biotechnol* 18:509-514 (2000)). This line will be transfected with a human frizzled 2 expression vector and selected in neomycin. The expression vector will be made by excising the frizzled 2 containing insert from one expression vector with NdeI and BamHI and ligating the insert into pcDNA3 (Invitrogen) which has a CMV promoter and a neomycin selection cassette. Thirty-two female C57B1/6 mice will be divided into groups of 8 mice each. They will be injected in the dermis of the tail with a combination of 50 μg plasmid encoding a costimulator and 50 μg linker plasmid diluted in normal saline at weeks zero, one and two. A group with empty vector is included as a negative control. On day 28 the mice will be injected subcutaneously in the flank with $20 \times 10^6$ frizzled 2 transfected EL4 cells or untransfected cells (Cho, H. J. et al., "Immunostimulatory DNA-based vaccines induce cytotoxic lymphocyte activity by a T-helper cell-independent mechanism," *Nat Biotechnol* 18:509-514 (2000)). The mice will be monitored three times a week for weight, and tumor growth measured with a caliper. Tumor volume is calculated by length×width$^2$×π/6 previously described (Radulovic, S. et al., "Inhibition of growth of HT-29 human colon cancer xenografts in nude mice by treatment with bombesin/gastrin releasing peptide antagonist (RC-3095)," *Cancer Res* 51:6006-6009 (1991)). Mice will be sacrificed four weeks post tumor challenge or if the tumor burden reaches approximately 2000 mm$^3$. Inhibition of tumor growth will be determined by ANOVA.

The polyclonal antibodies that are generated by the immunization strategies may exhibit binding, but may not be sufficiently concentrated in the polyclonal serum to have a biologic effect. The serum from several immunization strategies may need to be tested in vitro for their potential therapeutic utility before proceeding with the in vivo active immunization strategy for tumor prevention. The inhibition of tumor growth in the murine model may be due to cellular responses as well as humoral, which will lead to further investigations. These assays may be useful in determining if the frizzled expressing cell lines are susceptible to anti-proliferative activity of polyclonal anti-frizzled IgG.

Example 6

Overexpression of Wnt 14 and 16

Based upon sequences in the public human DNA gene database, we prepared gene-specific primers for all the known human wnt and frizzled genes. We obtained mRNA from primary human chronic lymphocytic leukemia cells or normal human lymphocytes. Using real time PCR, we then compared the relative expression of the wnt and frizzled genes in the normal and malignant lymphocytes, compared to the control genes GAPDH and 18S mRNA. We discovered that wnt 16 was 70-100 fold overexpressed in the malignant lymphocytes. Wnt 14 was 400 fold overexpressed in the malignant lymphocytes. We sequenced the amplicons to determine their identities. Northern blots of normal human tissues confirmed the lack of significant expression of wnt 16 mRNA in non-lymphoid cells and in peripheral blood lymphocytes. Following the procedures described above, we will confirm the overexpression of wnt 16 and wnt 14 protein in the malignant cells using non-crossreactive antibodies, and will test the effects of the anti-wnt 16 and anti-wnt 14 antibodies on cell survival in vitro, using normal lymphocytes as a control. In addition, upon review of our results, we can develop these antibodies and antigens as therapeutic agents.

Example 7

Regulation of Lymphocyte Survival by Integrins

The survival of lymphocytes requires that they interact with the extracellular matrix proteins produced by stromal cells in their surrounding microenvironment. These interactions may render the cells resistant to spontaneous and drug-induced apoptosis. VLA4 integrin-mediated cell adhesion is known to be involved in regulating cell survival in some leukemic cell lines. We are studying integrin effects on the survival of primary blood lymphocytes. Our data show that the α4-CS 1 fragment of fibronectin significantly improves the survival of blood lymphocytes. To develop a potential therapeutic strategy that combines integrin antagonists with cytotoxic drugs, we are investigating the mechanism of several integrin α4-specific antagonists. These compounds specifically inhibit the adhesion of B chronic lymphocytic leukemia cells to fibronectin. We are currently studying the signaling events affected by these integrin antagonists in primary human lymphocytes.

Example 7

Wnt Gene Expression in Normal and Malignant Lymphocytes

The secreted proteins of the diverse wnt gene family are known to play an important role in cell growth and differentiation. Evidence suggests that wnt signaling may regulate apoptosis. The purpose of these experiments is to identify the wnt genes that are most highly expressed in resting lymphocytes, and then to determine their potential role in cell survival.

Total RNA was prepared and treated with RNase-free DNase. The cDNA was synthesized from 5 μg total RNA using Superscript reverse transcriptase and oligo dT. To assure that there was no genomic DNA contamination, controls in which no reverse transcriptase was added were also carried out. TaqMan real-time PCR was performed using an ABI PRISM 7700 sequence Detector. Primers and probes for 46 wnt family members and their related genes were designed using Primer Express version 1.0 (Applied Biosystems). The reaction conditions were as follows: 2 min at 500 C (one cycle), 10 min at 950 C (one cycle), and 15s at 950 C and 1 min at 600 C (45 cycles). Two replicates for each gene were performed.

Having developed and validated a TaqMan real-time PCR assay to quantify the gene expression profiles of the wnt family and its related genes, we measured the gene expression profile in three B-CLL, two normal peripheral blood lymphocyte populations, and one purified B cell sample. We found that wnt6, wnt14 and wnt16 were overexpressed in B-CLL, compared to normal PBL or purified B cells. Wnt14 mRNA levels in B-CLL were 16-178 times those of PBL and B cell samples. The concentration of wnt6 mRNA in B-CLL samples was 8-32 fold higher than that in normal PBL and B-CLL samples. Wnt16 mRNA was expressed at 32-178 higher levels in B-CLL than in PBL. For other wnt-related families, such as Fzd, Frp, Wisp and DKK, we did not observe any significant differences. Thus, the wnt gene overexpression appears to be unique.

We have established a model system to study the integrin-dependent interaction of primary human lymphocytes with extracellular matrix proteins, and have shown that the binding promotes cell survival. We can now test the effects of integrin antagonists on cell signaling and apoptosis in both normal and malignant cells.

Other experiments revealed three wnt genes that are overexpressed in lymphocytes of patients with B-CLL, compared to normal peripheral blood lymphocytes. Since wnt proteins are secreted, they may function as survival factors for the malignant cells.

The specificities of the feeder cell-lymphocyte interactions that delay senescence and apoptosis are identified by using purified lymphocyte subpopulations (CD4, T cells, CD8, T cells, B cells), co-culturing with different feeder cells (monocytes, dendritic cells, endothelial cells, fibroblasts), and then measuring both spontaneous and drug-induced apoptosis.

The specific surface molecules and/or secreted factors responsible for the extended survival of the lymphocytes are identified by testing the effects of blocking antibodies against surface antigens on the feeder cells and the lymphocytes, determining the effect of neutralizing antibodies against cytokines and growth factors, and generating sense and antisense transfectomas of feeder cells to confirm the roles of the specific interaction revealed in the first two methods described.

The intracellular signaling pathways in quiescent lymphocytes that are altered by contact with feeder cells, and that increase their survival are identified by determining levels and phosphorylation status of proteins in key activation pathways (mitogen activated protein kinase, STATs, NF-Kb, b-catenin), assessing levels and phosphorylation status of proteins that regulate apoptosis (bcl2 family members, caspases, IAPB, SMAC/DIABLO), and testing the effects of pharmacologic inhibitors of signal transduction on the survival of quiescent lymphocytes cultivated with feeder cells, alone or in combination with cytotoxic agents.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention, as set forth in the claims which follow. All publications or patent documents cited in this specification are incorporated herein by reference as if each such publication or document was specifically and individually indicated to be incorporated herein by reference.

Citation of the above publications or documents is not intended as an admission that any of the foregoing is pertinent prior art, nor does it constitute any admission as to the contents or date of these publications or documents.

We claim:

1. A method of inhibiting the proliferation or survival of head and neck squamous cell carcinoma cells that require overexpression of a Wnt-1 protein in a Wnt/zd signaling pathway for proliferation or survival, wherein the carcinoma cells overexpress the Wnt-1 protein when compared to non-carcinoma cells of the same cell type, said method comprising contacting the carcinoma cells with an anti-Wnt-1 antibody that inhibits the Wnt/zd signaling pathway in the carcinoma cells.

2. The method according to claim 1, wherein the anti-Wnt-1 antibody is an antagonist of the Wnt/zd signaling pathway.

3. A method of inhibiting the proliferation or survival of head and neck squamous cell carcinoma cells that overexpress a Wnt-1 protein when compared to non-carcinoma cells of the same cell type, said method comprising contacting the carcinoma cells with an anti-Wnt-1 antibody that facilitates carcinoma cell toxicity or killing by complement.

4. A method of inhibiting the proliferation or survival of head and neck squamous cell carcinoma cells that overexpress a Wnt-1 protein when compared to another Wnt protein in the same carcinoma cells, said method comprising contacting the carcinoma cells with an anti-Wnt-1 antibody that facilitates carcinoma cell toxicity or killing by complement.

5. A method of inhibiting the proliferation or survival of head and neck squamous cell carcinoma cells, that require overexpression of a Wnt-1 protein in a Wnt/zd signaling pathway for proliferation or survival, wherein the carcinoma cells overexpress the Wnt-1 protein when compared to non-carcinoma cells of the same cell type and wherein the Wnt-1 protein is overexpressed when compared to another Wnt protein in the same carcinoma cells, said method comprising contacting the carcinoma cells with an anti-Wnt-1 antibody that inhibits the Wnt/zd signaling pathway in the carcinoma cells.

6. The method according to claim 5, wherein the anti-Wnt-1 antibody is an antagonist of the Wnt/zd signaling pathway.

* * * * *